(12) United States Patent
Hosny et al.

(10) Patent No.: US 12,183,468 B1
(45) Date of Patent: Dec. 31, 2024

(54) METHODS AND SYSTEMS FOR DETERMINING HEALTH OF AN ORGAN BASED ON MEDICAL IMAGE DATA USING ARTIFICIAL INTELLIGENCE

(71) Applicant: Ambient, Inc., Brookline, MA (US)

(72) Inventors: Ahmed Sherif Fouad Hosny, San Francisco, CA (US); Hugo J Aerts, Brookline, MA (US)

(73) Assignee: Ambient, Inc., Brookeline (MA)

( * ) Notice: Subject to any disclaimer, the term of this patent is extended or adjusted under 35 U.S.C. 154(b) by 0 days.

(21) Appl. No.: 18/824,547

(22) Filed: Sep. 4, 2024

(51) Int. Cl.
| | | |
|---|---|---|
| *G16H 50/30* | (2018.01) | |
| *G06V 10/25* | (2022.01) | |
| *G06V 10/764* | (2022.01) | |
| *G16H 20/00* | (2018.01) | |
| *G16H 30/20* | (2018.01) | |
| *G16H 30/40* | (2018.01) | |

(52) U.S. Cl.
CPC ........... *G16H 50/30* (2018.01); *G06V 10/25* (2022.01); *G06V 10/764* (2022.01); *G16H 20/00* (2018.01); *G16H 30/20* (2018.01); *G16H 30/40* (2018.01)

(58) Field of Classification Search
None
See application file for complete search history.

(56) References Cited

U.S. PATENT DOCUMENTS

| | | | | |
|---|---|---|---|---|
| 2017/0293725 A1* | 10/2017 | Liu | .................. | G06F 16/3329 |
| 2021/0233251 A1* | 7/2021 | Rothrock | ............... | G06N 20/00 |
| 2021/0407078 A1* | 12/2021 | Samavati | ................. | G06N 3/04 |
| 2022/0028058 A1* | 1/2022 | Mohamed | ............. | G06F 18/214 |
| 2023/0144137 A1* | 5/2023 | Kapur | .................... | G16H 30/40 382/103 |
| 2023/0290111 A1* | 9/2023 | Kunz | ..................... | G06N 5/022 |
| 2024/0177838 A1* | 5/2024 | Liu | ........................ | G16H 50/70 |
| 2024/0257497 A1* | 8/2024 | Goldenberg | ........... | G06V 10/82 |
| 2024/0290076 A1* | 8/2024 | Hosseinzadeh Taher | .................. | G06V 10/82 |

OTHER PUBLICATIONS

Ayesha, et al. "Automatic medical image interpretation: State of the art and future directions" Pattern Recognition, vol. 114, 2021, 107856. (Year: 2021).*

* cited by examiner

*Primary Examiner* — Jonathan Ng
(74) *Attorney, Agent, or Firm* — Bajwa IP Law Firm; Haris Zaheer Bajwa

(57) ABSTRACT

A method for determining the health of an organ, specifically the thymus, using medical image data is disclosed. The method involves generating a foundation model by retrieving and pre-processing a set of images related to various organs, including CT scans of the thymus. A deep convolutional neural network is then used to produce embedding vectors, which are refined through a self-supervised learning framework. A task-specific classifying model is generated, comprising a Quality Control (QC) model and a score model. The QC model provides binary predictions differentiating between normal thymus degradation and abnormalities, while the score model evaluates fat and soft tissue levels in the thymus. The health of a potential organ is evaluated by receiving a CT of an organ to be evaluated, generating an embedding vector using the foundation model, and applying the task-specific classifying model to produce a health score. Clinical solutions, including chemotherapy and immunotherapy are then applied based on the health score.

16 Claims, 9 Drawing Sheets

METHODS AND SYSTEMS FOR DETERMINING HEALTH OF AN ORGAN BASED ON MEDICAL IMAGE DATA USING ARTIFICIAL INTELLIGENCE

TECHNICAL FIELD

The invention relates to the field of immunology and medical diagnostics based on image data. More specifically, the invention relates to methods and systems for evaluating an individual's immune health status using biomarkers derived from medical imaging data and utilizing Artificial Intelligence and Cognitive Computing systems to conduct a non-invasive image analysis of organ health.

BACKGROUND

The immune system is a complex network that defends the body against disease-causing organisms (pathogens) and eliminates abnormal cells, including those that can develop into cancer. The status of an individual's immune health is linked to the incidence and treatment response of various diseases, such as immune-related disorders, cancer, and certain types of cardiovascular disease.

In cancer treatment, the immune system's role is critical, particularly with the advent of cancer immunotherapies. These therapies, such as FDA-approved anti-PD-1/anti PD-L1 treatments for melanoma and non-small cell lung cancer (NSCLC), enhance the immune response to target and destroy tumor cells. Despite their success, the clinical benefits are limited to a subset of patients. Given the high costs and potential toxicity of immunotherapy, there is an urgent need for biomarkers to distinguish responders from non-responders before treatment.

Current research is exploring various biomarkers, including programmed death-ligand 1 (PD-L1) levels, genetic mutation profiles like total mutational burden (TMB), and the presence of tumor-infiltrating lymphocytes (TIL) and cytokines. However, these biomarkers often fall short, as they typically rely on biopsies that capture only a small, potentially non-representative part of the tumor. Blood-based biomarkers, such as T lymphocytes, the T-cell receptor repertoire, myeloid-derived suppressor cells, and circulating tumor cells, offer a potential alternative, though research in this area is still in its early stages. Thus, there is a pressing need for improved biomarkers to optimize treatment decisions.

The immune system also plays a significant role in cardiovascular disease (CVD). The cardiovascular and immune systems are interlinked, with immune characteristics influencing plaque formation in vessels. Consequently, biomarkers of immune health are also sought in the CVD field to enhance risk prediction and patient stratification.

Medical imaging holds significant potential for biomarker development. Unlike traditional biopsy-based assays, medical imaging can provide comprehensive insights into a patient's health, including immune-related organs, the cardiovascular system, total tumor burden (including primary and metastatic sites), lung health, and body composition.

Recent advances in artificial intelligence (AI) and computational algorithms are addressing many challenges in medical imaging. Key factors contributing to these AI breakthroughs include increased computational power, advancements in deep-learning algorithms, and the availability of open-source deep-learning platforms. These developments have enabled the automatic quantification of complex patterns in images, facilitating the creation of imaging-based biomarkers.

Despite these advancements, there remains a need for reliable methods to evaluate an individual's immune system health, which can be critical for determining appropriate treatments. This invention aims to address this need by leveraging advanced medical imaging and AI to develop novel biomarkers for immune health assessment.

SUMMARY

This summary is intended to provide an overview of the subject matter of the present disclosure, and is not intended to identify essential elements or key elements of the subject matter, nor is it intended to be used to determine the scope of the claimed implementations. Its sole purpose is to present some concepts of one or more exemplary aspects in a simplified form as a prelude to the more detailed description that is presented later. The proper scope of the present disclosure may be ascertained from the claims set forth below in view of the detailed description below and the drawings.

One or more exemplary embodiments describe an exemplary method for evaluating health of an organ, comprising receiving medical image data associated with an organ, the organ comprising a thymus, the medical image data comprising a computed tomography scan. and preparing a finalized image by applying pre-processing, using one or more processors, to the medical image data. In an exemplary embodiment, exemplary method may further include generating an embedding vector by applying a foundation model on the finalized image, the foundation model encoding the finalized image data based on a previously trained foundation model, the previously trained foundation model generated utilizing a deep convolutional neural network and a self-supervised learning model on a plurality of set of images associated with a plurality of thymus, and further generating a classification output by applying a classifying model on the embedding vector, wherein the classifying model comprises of a Quality Control (QC) model and a score model, the QC model comprising a trained logistic regression model providing binary predictions with probabilities differentiating between normal thymus degradation and abnormalities, and wherein the score model comprising another trained logistic regression model evaluating a level of fat and soft tissue in the thymus, the QC model and the score model generated utilizing a set of labeled images associated with respective thymus. outputting a health score based on the classification output, and applying a clinical solution based on the health score.

One or more exemplary embodiments describe an exemplary method for evaluating health of an organ, comprising receiving medical image data associated with an organ, the organ comprising a thymus, the medical image data comprising a computed tomography scan, preparing a finalized image by applying pre-processing to the medical image data, generating a classification output by applying a machine learning model on the finalized image, the machine learning model trained based on a set of images associated with a plurality of thymus, at least a number of the set of images comprising labeled images, the labeled images labeled to indicate levels of fatty degeneration or non-fat attenuation in the thymus, the machine learning model generated utilizing at least supervised learning techniques, and outputting a health score based on the classification output.

One or more exemplary embodiments describe an exemplary method for determining health of an organ based on medical image data, comprising generating a foundation model, by retrieving a set of images related to a plurality of organs, the set of images comprising CT scans related to respective thymus, generating a set of pre-processed images by applying pre-processing to the set of images, the pre-processing comprising standardizing the set of images to an isotropic resolution and adjusting scan intensities for consistency, training the foundation model to predict embedding vectors by producing embedding vectors for each image of the set of pre-processed images by utilizing a deep convolutional neural network architecture, and refining the embedding vectors by applying a self-supervised learning framework to the embedding vectors associated with the set of pre-processed images, generating a task-specific classifying model based, wherein generating the task specific classifying model comprising generating a Quality Control (QC) model and generating a score model, the QC model providing binary predictions with probabilities differentiating between normal thymus degradation and abnormalities, wherein the score model evaluating a level of fat and soft tissue in the thymus, by retrieving a second set of images associated with another plurality of organs and associated medical data, the associated medical data comprising labels indicating health of organs, generating embedding vectors for each image of the respective second set of images by applying the foundation model, generating the QC model based on embedding vectors of each respective image of the second set of images and associated medical data, and generating the score model based on embedding vectors of each respective image of a chosen set of the second set of images and associated medical data, evaluating health of a potential organ based on medical image data, comprising receiving medical image data of the potential organ, the potential organ comprising a thymus, the medical image data comprising a computed tomography scan, and generating a finalized image by applying pre-processing to the received medical image data, generating an embedding vector by applying the foundation model on the finalized image, and generating a classification output by applying the task-specific classification model on the embedding vector, wherein the task-specific classification model comprises of a Quality Control (QC) model and a score model, wherein generating the classification output comprises generating the classification output based on an inflammation label output by the QC model and based on the level of fat and soft tissue label output by the score model based on the embedding vector, and outputting the health score based on the generated classification output, applying a clinical solution based on the health score, comprising applying chemotherapy and immunotherapy in response to a low health score, the low health score comprising less than 33 percent of a possible highest score of the health score, and applying immunotherapy in response to a high health score, the high health score comprising greater than 68 percent of a possible highest score of the health score.

One or more exemplary embodiments describe an exemplary method for evaluating health of an organ based on medical image data, comprising generating a foundation model, by retrieving a set of images related to a plurality of organs, the set of images comprising CT scans related to respective thymus, generating a set of pre-processed images by applying pre-processing to the set of images, training the foundation model to predict embedding vectors, using artificial intelligence, by producing embedding vectors for each image of the set of pre-processed images by utilizing a deep convolutional neural network architecture, and refining the embedding vectors by applying a self-supervised learning framework to the embedding vectors associated with the set of pre-processed images. The exemplary method may further include generating a task-specific classification model, wherein generating the task specific classification model comprises generating a Quality Control (QC) model and generating a score model, the QC model providing binary predictions with probabilities differentiating between normal thymus degradation and abnormalities, wherein the score model evaluating a level of fat and soft tissue in the thymus, by retrieving a second set of images associated with another plurality of organs and associated medical data, the associated medical data comprising labels indicating health of organs, generating embedding vectors for each image of the respective second set of images by applying the foundation model, generating the QC model based on embedding vectors of each respective image of the second set of images and associated medical data, and generating the score model based on embedding vectors of each respective image of a chosen set of the second set of images and associated medical data. The method may further comprise evaluating health of a potential organ based on the medical image data, comprising receiving the medical image data of the potential organ, the potential organ comprising a thymus, the medical image data comprising a computed tomography scan, generating a finalized image by applying pre-processing to the received medical image data of the potential organ, and generating an embedding vector by applying the foundation model on the finalized image, and generating a classification output by applying the task-specific classification model on the embedding vector, wherein the task-specific classification model comprises of a Quality Control (QC) model and a score model, wherein generating the classification output comprises generating the classification output based on an inflammation label output by the QC model and based on the level of fat and soft tissue label output by the score model based on the embedding vector, and outputting a health score based on the generated classification output.

This Summary is provided to introduce a selection of concepts in a simplified form; these concepts are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

The novel features which are believed to be characteristic of the present invention, as to its structure, organization, use and method of operation, together with further objectives and advantages thereof, will be better understood from the following drawings in which a presently preferred embodiment of the present disclosure will now be illustrated by way of example. It is expressly understood, however, that the drawings are for the purpose of illustration and description only and are not intended as a definition of the limits of the present disclosure. Embodiments of the present disclosure will now be described by way of example in association with the accompanying drawings in which.

DETAILED DESCRIPTION

Figure 1:
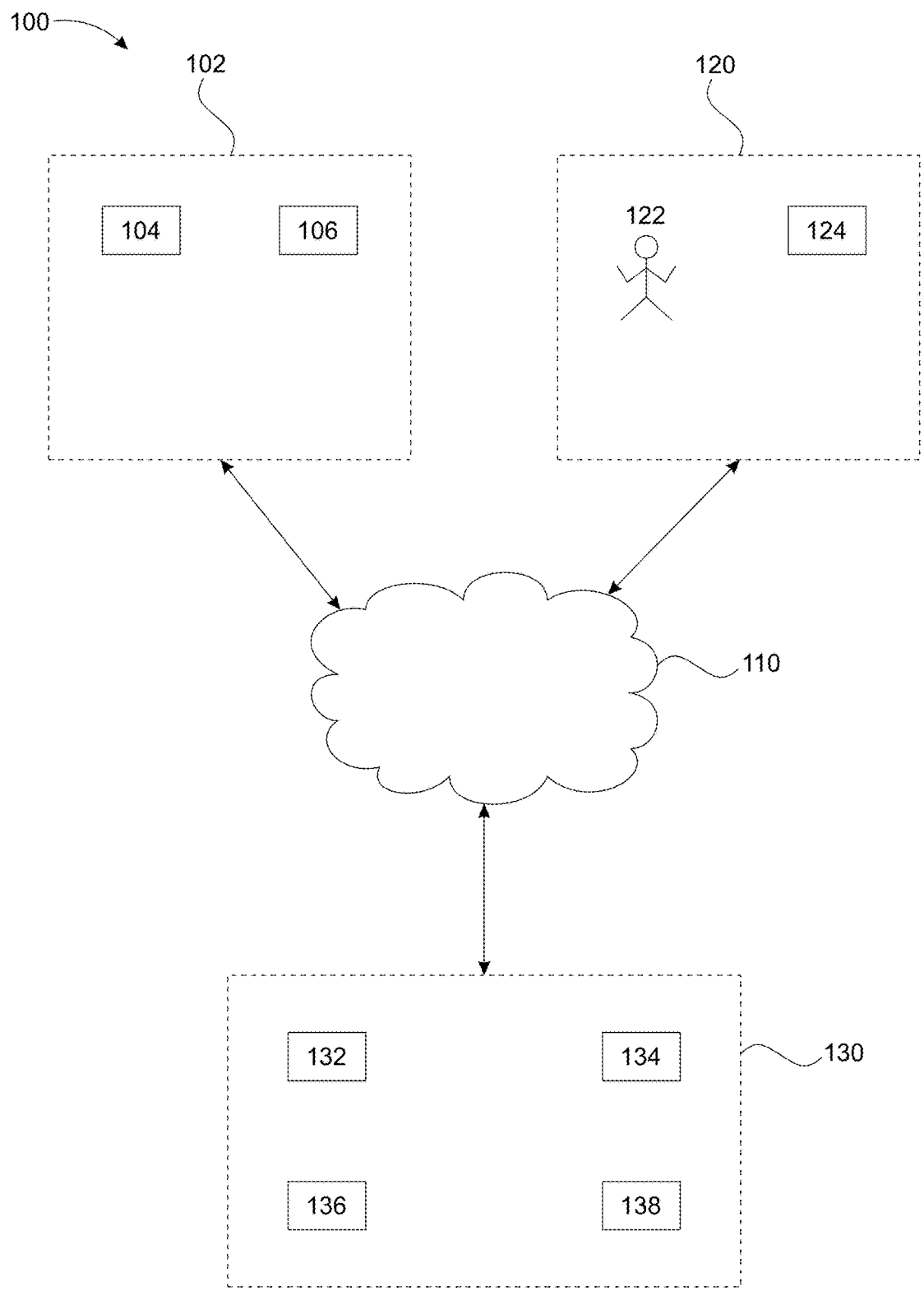
FIG. 1 shows a block diagram of an exemplary system for determining health of an organ based on medical acquisition data, consistent with one or more exemplary embodiments of the present disclosure.

The novel features which are believed to be characteristic of the present invention, as to its structure, organization, use and method of operation, together with further objectives and advantages thereof, will be better understood from the following discussion.

As a preliminary matter, some of the figures describe concepts in the context of one or more structural components, variously referred to as functionality, modules, features, elements, etc. The various components shown in the figures can be implemented in any manner, for example, by software, hardware (e.g., discrete logic components, etc.), firmware, and so on, or any combination of these implementations. In one embodiment, the various components may reflect the use of corresponding components in an actual implementation. In other embodiments, any single component illustrated in the figures may be implemented by a number of actual components. The depiction of any two or more separate components in the figures may reflect different functions performed by a single actual component. The figures discussed below provide details regarding exemplary systems that may be used to implement the disclosed functions.

Some concepts are described in the form of steps of a process or method. In this form, certain operations are described as being performed in a certain order. Such implementations are exemplary and non-limiting. Certain operations described herein can be grouped together and performed in a single operation, certain operations can be broken apart into plural component operations, and certain operations can be performed in an order that differs from that which is described herein, including a parallel manner of performing the operations. The operations can be implemented by software, hardware, firmware, manual processing, and the like, or any combination of these implementations. As used herein, hardware may include computer systems, discrete logic components, such as application specific integrated circuits (ASICs) and the like, as well as any combinations thereof.

As to terminology, the phrase "configured to" encompasses any way that any kind of functionality can be constructed to perform an identified operation. The functionality can be configured to perform an operation using, for instance, software, hardware, firmware and the like, or any combinations thereof.

As utilized herein, terms "component," "system," "client" and the like are intended to refer to a computer-related entity, either hardware, software (e.g., in execution), and/or firmware, or a combination thereof. For example, a component can be a process running on a processor, an object, an executable, a program, a function, a library, a subroutine, and/or a computer or a combination of software and hardware.

By way of illustration, both an application running on a server and the server can be a component. One or more components can reside within a process and a component can be localized on one computer and/or distributed between two or more computers. The term "processor" is generally understood to refer to a hardware component, such as a processing unit of a computer system.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any non-transitory computer-readable device, or media.

Non-transitory computer-readable storage media can include but are not limited to magnetic storage devices (e.g., hard disk, floppy disk, and magnetic strips, among others), optical disks (e.g., compact disk (CD), and digital versatile disk (DVD), among others), smart cards, and flash memory devices (e.g., card, stick, and key drive, among others). In contrast, computer-readable media generally (i.e., not necessarily storage media) may additionally include communication media such as transmission media for wireless signals and the like.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

Exemplary methods and systems allow for a single CT scan analysis of an organ, and therefore does not require prolonged exposure. That is, exemplary systems and methods provide insight into the health and responsiveness of an exemplary organ based on one singular scan of an organ to aid in making a decision on clinical steps. Therefore, in an exemplary embodiment, exemplary methods and systems provide a non-invasive, accurate, and fast approach for diagnosing a health status of an organ, in addition to predicting success rates of potential outcomes of clinical approaches in various organs.

Exemplary application of artificial intelligence to assist with image analysis leads to an exemplary automated and accurate health classification system. Exemplary classification and predictions may serve as a clinically valuable tool in determining health of an organ, determining approaches on monitoring of a respective organ, and predicting impact of various clinical steps. Therefore, exemplary classification systems aid in improving patient outcomes.

In an exemplary embodiment, a potential organ may be evaluated and its properties may be analyzed utilizing predictive models generated utilizing artificial intelligence. That is, medical image data, such as a CT scan may be captured related to a patient's organ, such as a thymus. In an exemplary embodiment, an exemplary CT scan may focus on the thymus and the thymus may be analyzed.

In an exemplary embodiments, exemplary embodiments and exemplary scenarios described in the detailed description, focus on thymus as an organ for evaluation of health, that is, images related to thymuses are acquired, a radiologist (or an expert) labels based on condition apparent in an exemplary medical image, models are generated related to thymuses, and exemplary models are applied to a medical image of a thymus to evaluate, producing classifications and/or exemplary health scores. However, similar principles may be applied, for additional organs and/or combination of organs, that is, a data set of organ images, a second data set of organs images with labels (which may be part of a first data set of images), may be utilized along with the labeling to create exemplary models and subsequently, evaluate organ of the same type from which the models were created, including spleen, kidneys, lungs, heart, bone marrow, etc.

Utilizing exemplary parameters for both processing and analyzing images as discussed in further detail below, artificial intelligence may be utilized to determine the health quality of a potential organ by utilizing exemplary generated AI models. In an exemplary embodiment, an exemplary health score or prediction may be provided based on application of exemplary classification models. Additionally, exemplary supportive metrics may be provided, which may include chance of success and confidence in prediction, aiding a clinician in providing advice and guidance to potential patients on medical approaches.

In an exemplary embodiment, a clinician may therefore decide whether to apply immunological approaches, chemotherapy approaches, surgical approaches, radiotherapy approaches, and combination thereof, or neither.

Referring now to the figures, FIG. 1 shows a block diagram of an exemplary system 100 for determining health of an organ based on medical acquisition data, consistent with one or more exemplary embodiments of the present disclosure. In an exemplary embodiment, system 100 includes a healthcare facility environment 102, network 110, physician environment 120, and service provider environment 130.

One of ordinary skill in the art would recognize that any of the elements of health care facility environment 102 and physician environment 120 may be present in the other, or they may simply function as a singular environment.

In an exemplary embodiment, health care facility environment 102 may include medical image capturing device 104, such as devices for X-ray Radiography, Computed Tomography (CT), Magnetic Resonance Imaging (MRI), Ultrasound, Positron Emission Tomography, Single Photon Emission Computed Tomography (SPECT), Fluoroscopy, Mammography, Bone Densitometry (DEXA or DXA), Angiography, Endoscopy, Thermography, Optical Coherence Tomography (OCT), Elastography, and Photoacoustic Imaging, etc. In an exemplary embodiment, health care facility environment may further contain processors 106 and databases 108. In an exemplary embodiment, databases 108 may be utilized to store information and data including medical records, health records, billing, image data, etc. In an exemplary embodiment, processors 106 may be utilized for communicating with external sources, managing health data, interaction with medical image capturing device 104, and additional processes as described with further detail in context of FIG. 6. In an exemplary embodiment, processors 106 may allow for labeling of captured images. In an exemplary embodiment, details regarding labeling are provided in further detail below.

In an exemplary embodiment, all elements within system 100 may be connected to an electronic network 100, such as the Internet, through one or more computers, servers, and/or handheld mobile devices.

In an exemplary embodiment, physician environment 120 physician 122 may create or otherwise obtain images of one or more patients' organs. Furthermore, in an exemplary embodiment physician 122 may also obtain any combination of patient-specific information, such as age, medical history, blood pressure, blood viscosity, etc. Combination of processors 124 and databases 126 that are part of physician environment may be utilized to enter and store medical records, transmit information/data, communicate with external entities, view reports, request medical reports, send prescriptions, and/or send instructions to patients.

In an exemplary embodiment, physician 122 or an entity may transmit medical image data (for example, CT scan) and/or patient-specific information to service provider environment 130, along with a request for a health score or a health score report.

In an exemplary embodiment, service provider environment 130 may have databases 132 for storing data, including data for storing images and data received from physician 122 or any other sources. In an exemplary embodiment, databases 132 may further store models generated utilizing artificial intelligence which may be constantly updated and may be utilized to evaluate additional data received by processors 134. Furthermore, service provider environment 130 may further include processors 134 which may comprise processing devices for processing images and data stored in the storage devices. In an exemplary embodiment, service provider environment 130 may provide a physician, an ERM, or other entity with a health report which may include an exemplary health score based on received medical image data for evaluation.

In an exemplary embodiment, alternatively or in addition, embodiments of the present disclosure (or portions of the embodiments of exemplary system and methods of the present disclosure) may be performed on a local processing device (e.g., a laptop), absent an external server or network.

Figure 2:
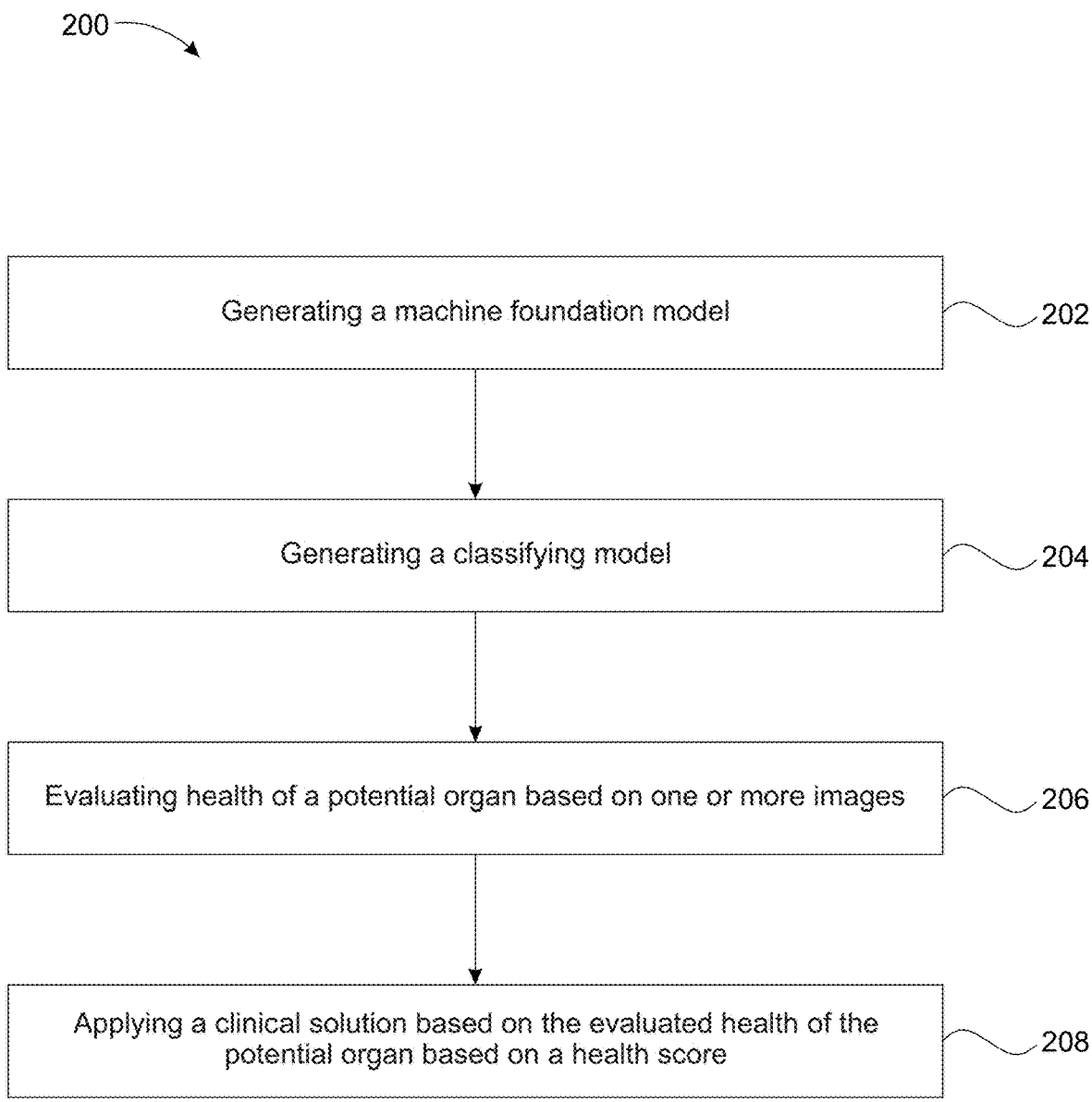
FIG. 2 shows an exemplary method for evaluating and treating an organ, consistent with one or more exemplary embodiments of the present disclosure

FIG. 2 shows an exemplary method for evaluating and treating an organ, consistent with one or more exemplary embodiments of the present disclosure. In an exemplary embodiment, exemplary method of FIG. 2 may be performed within system 100 of FIG. 1.

Figure 3A:
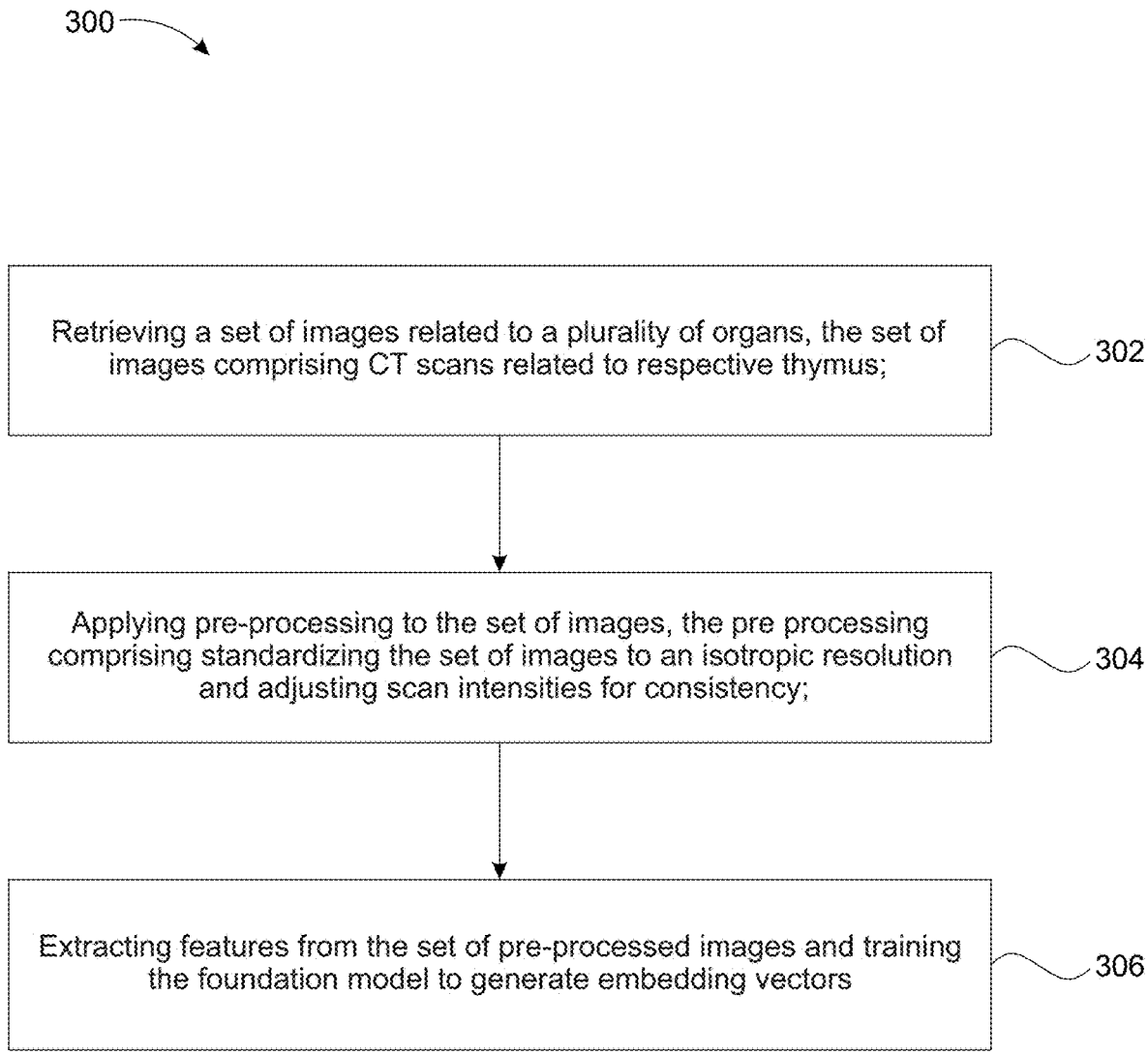
FIG. 3A shows an exemplary method for generating a machine foundation model, consistent with one or more exemplary embodiments of the present disclosure.
Figure 3B:
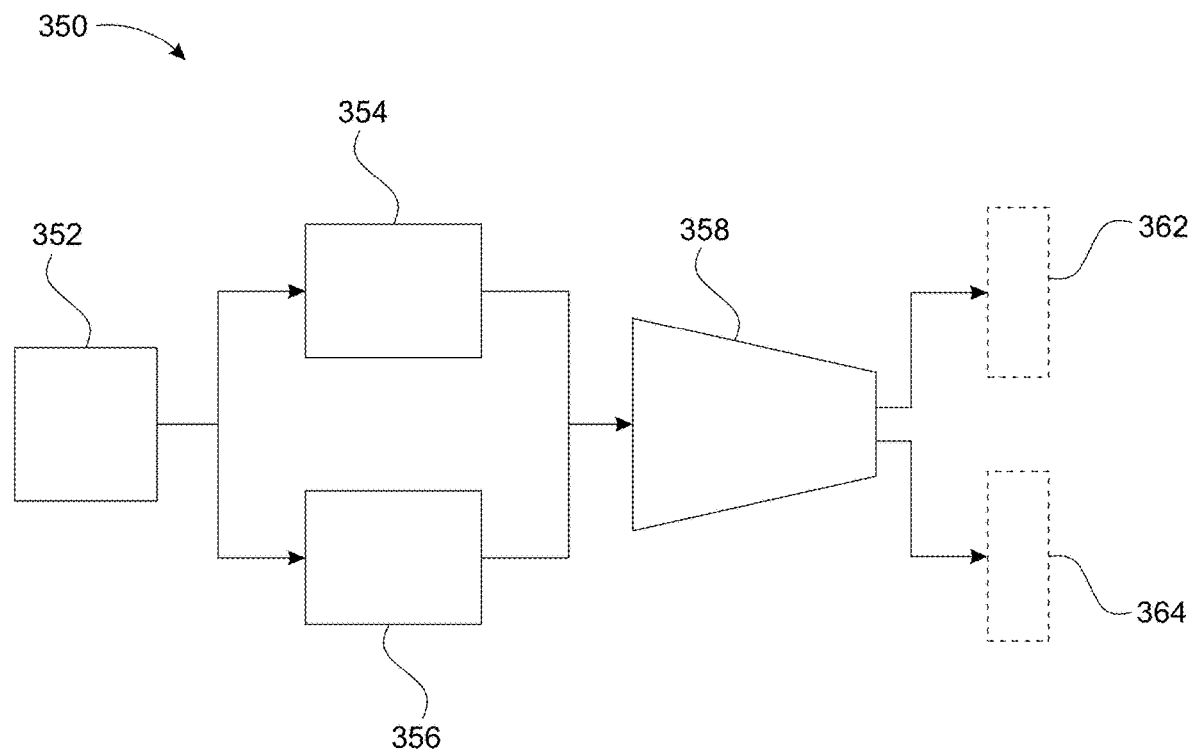
FIG. 3B illustrates a block diagram of a training phase of a foundation model for determining health of an organ, consistent with one or more exemplary embodiments of the present disclosure.

In an exemplary embodiment, method 200 may comprise of step 202. In an exemplary step 202 may comprise of generating a machine foundation model. Details of step 202 are provided in context of method 300 as presented in FIG. 3A, which provides details of generating a machine foundation model consistent with one or more exemplary embodiments of the present disclosure. Method 300 may be understood in context of FIG. 3B which illustrates a block diagram of a training phase of a foundation model for determining health of an organ, consistent with one or more exemplary embodiments of the present disclosure.

In an exemplary embodiment, method 300 may comprise of step 302. In an exemplary embodiment, step 302 may comprise retrieving, from one or more databases, a set of images related to a plurality of organs. In an exemplary embodiment, respective sets of images related to a plurality of organs may refer to respective sets of different images related to a same type of organ, that is, for example, thymus, spleen, etc. etc. In an exemplary embodiment, the set of images may comprise data related to CT scans but may also include image data related to any type of medical image data that may be captured including MRIs, X-Rays, etc.

In an exemplary embodiment, the images may be captured with an image capturing device, such as image capturing device 104, which may be an exemplary CT machine. In an exemplary embodiment, image capturing techniques are not completely standardized, and there is a significant technician-dependent variability, but there are accepted general guidelines on how to capture scans or images on CT machines. Therefore, exemplary CT images may be captured in a standardized manner.

In an exemplary embodiment, method 300 may further comprise step 304. In an exemplary embodiment, step 304 may comprise applying pre-processing to the set of images. In an exemplary embodiment, one or more processors 134 may apply pre-processing to the sets of images. In an exemplary embodiment, pre-processing may comprise standardizing the set of images to an isotropic resolution and adjusting scan intensities for consistency In an exemplary embodiment, applying pre-processing may include cropping an image so that an exemplary object of interest (ROI) in the center. For example, an exemplary CT scan may be cropped to a focus on an area around an exemplary thymus, measuring 50 mm×50 mm×75 mm.

In an exemplary embodiment, CT images and corresponding manually contoured thymus may be preprocessed by resampling the images to an isotropic 1 mm spatial resolution and normalizing 3D pixel (voxel) values by mapping a range of −1024 to 3048 Hounsfield units (HU) between 0 and 1.

In an exemplary embodiment, standardizing all the captured images to user defined or automatically generated parameters may be valuable in terms of improving predictive accuracy.

In an exemplary embodiment, creating a clean and unbiased dataset may serve as a critical part of developing a robust predictive model. A clean and unbiased data set may refer to both image quality and data linking, that is, an accurate record of images. In an exemplary embodiment, any images with undesirable qualities such as debris, shadowing, poor exposure, etc., may be removed from respective datasets. In an exemplary embodiment, images that are sub-optimal, may be excluded. In an exemplary embodiment, artificial intelligence (as defined in further detail below with respect to step 306) may be utilized for pre-processing as appropriate.

In detail, to determine robust quality, pre-processing may entail determining that appropriate ROIs exist in captured images and appropriate organs are captured. For example, metadata may mislabel exemplary images (so an actual scan may not deal with a relevant organ) or a CT scan may not have a clear image of an organ due to presence of additional materials (such as pacemakers, etc.) or due to angle of captured CT scan. In these instances, scans that aren't acceptable may be eliminated. Accordingly, Artificial Intelligence may be utilized to determine that each image in the set of images is associated with a relevant type of organ for which an exemplary foundation model is being generated, for example, thymus.

In an exemplary embodiment, pre-processed images may be stored in one or more exemplary databases, such as databases 132.

In an exemplary embodiment, method 300 may further comprise step 306. In an exemplary embodiment, step 306 may comprise training the foundation model to predict embedding vectors, using artificial intelligence, based on the set of pre-processed images. In an exemplary embodiment this may entail producing embedding vectors for each set of pre-processed images by utilizing a deep convolutional neural network architecture, and refining the embedding vectors by applying a self-supervised learning framework to the embedding vectors associated with the set of pre-processed images.

In an exemplary embodiment, training the foundation model to predict embedding vectors may comprise extracting features from the set of pre-processed images and training the foundation model to generate embedding vectors, using artificial intelligence (AI).

In an exemplary embodiment, AI may refer to a software platform and computing system capable of analyzing image data. The exemplary platform may include elements of Deep Learning, Cognitive Computing, and Machine Learning.

In an exemplary embodiment, an exemplary deep convolutional neural network architecture which may be a type of model utilized in AI for processing and understanding data may be utilized to extract features from an exemplary set of pre-processed images. In an exemplary embodiment, an exemplary deep convolutional neural network architecture may be ResNet50, which may comprise of 50 layers, which may be configured to capture intricate patterns in data. In an exemplary embodiment, ResNet50 may process and encode images in high-dimensional embeddings.

In an exemplary embodiment, AI may further include Swapping Assignments between multiple Views (SwAV) which is a self-supervised learning method within AI, designed to learn representations of data without requiring labeled examples. In an exemplary embodiment, SwAV is an exemplary contrastive learning method, details of which are provided in further detail below. In an exemplary embodiment, SwAV may use embeddings from an exemplary deep convolutional neural network, to perform self-supervised learning by clustering and aligning multiple augmented views of the same image, ensuring that the learned features are robust and invariant to transformations.

In an exemplary embodiment, in further detail, applying SwAV entailing applying exemplary self-supervised contrastive learning may allow an exemplary foundation model to be trained to learn which regions within an organ, such as an exemplary thymus, are most important for accurately describing it, without human supervision or labeled data. In an exemplary embodiment, an exemplary foundation model may learn to encode images based on specific augmentations and transformations applied to them. In an exemplary embodiment, applying augmentation and transformation may comprise applying training approaches consistent with Swapping Assignments between Views (SwAV) framework, which is described in further detail below.

In an exemplary embodiment, for further details regarding the use of SwAV and ResNet50 encoder, an exemplary foundation model may be developed utilizing self-supervised contrastive learning, specifically the Swapping Assignments between Views (SwAV) framework. In an exemplary embodiment, an exemplary SwAV framework may employ a deep convolutional neural network, such as ResNet50 encoder, which may be pre-trained to learn representations by solving a swapped prediction problem. In such an exemplary scenario, representations from two views of a volume may be taken, and one is trained to predict the cluster of the other. In an exemplary embodiment, "view" may refer to an original volume augmented by a set of transformations unique to every view. In an exemplary embodiment, this approach may allow the model to learn high-dimensional mappings between views.

In an exemplary embodiment, in addition to solving the prediction problem, an exemplary foundation model may also learn to map views of different volumes to distinct clusters. In an exemplary embodiment, this dual objective may enable an exemplary model to capture the inherent radiographic properties of the thymus by clustering similar representations together and differentiating them from others.

In an exemplary embodiment, first an exemplary SwAV framework may be utilized to train the AI to recognize important features of the thymus. In an exemplary embodiment, SwAV framework works by creating different views of the same image through various transformations. In an exemplary embodiment, exemplary transformations include random-sized cropping in three dimensions, random affine transformations for translation and rotational invariances, random histogram shifts, and Gaussian smoothing for robustness to intensity shifts. In an exemplary embodiment, exemplary data augmentations may help the model learn detailed and nuanced features of the thymus organ.

Referring back to FIG. 3B, in which system 350 is displayed. An exemplary scenario is disclosed. In a training scenario, an exemplary image 352 may be provided. In an exemplary embodiment, image 352 may be rotated to have a transformed image 354 and another transformed image 356. In an exemplary embodiment, transformed image 354 may be image 352 rotated by 90 degrees and transformed image 356 may be image 352 rotated by 180 degrees. In an exemplary embodiment, transformed images 354 and 356 may be provided to respective encoder 358 which may generate respective outputs 362 and 364, wherein output 362 may be based on transformed image 354 and output 364 may be based on transformed image 356. In an exemplary embodiment, by maximizing agreement between outputs 362 and 364, an exemplary foundation model may maximize agreement. In an exemplary embodiment, additional transformations may be applied under SwAV framework to an exemplary input image, such as image 352, and agreement may be maximized to develop/train a model which may predict or generate embedding vectors. In an exemplary embodiment, encoder 358 may be a ResNet50.

In an exemplary embodiment, an exemplary convolution deep learning model, such as ResNet50 may be trained, which may be a type of neural network known as a convolutional neural network (CNN). In an exemplary embodiment, ResNet50 may be particularly effective for image recognition tasks because it has 50 layers, allowing it to learn very detailed and complex features from the images. In an exemplary embodiment, ResNet50 model may process the thymus area and may generate 4,096 features, which may be numerical representations capturing various abstract characteristics of the thymus. In an exemplary embodiment, exemplary deep learning model may be trained over 800 epochs using four Quadro RTX 8000 GPUs, a process that may take approximately 2 days. In an exemplary embodiment, an epoch may refer to passing of the entire dataset through the model. In an exemplary embodiment, a batch size of 128 data samples may be applied for each GPU, resulting in a total batch size of 512 data samples. In an exemplary embodiment, an exemplary training may utilize a stochastic gradient descent optimizer with a learning rate of 0.3, a weight decay of 1e-6, and a momentum of 0.9, along with a cosine annealing strategy for learning rate decay. Enhancements such as mixed precision training, distributed data-parallel techniques, and caching of cropped patches from large volumes may further be implemented to accelerate training.

In an exemplary embodiment, SwAV framework may be utilized with 4,096 output features and 300 prototypes, keeping the prototypes static during the initial epoch to ensure stability. In an exemplary embodiment, a temperature setting of 0.1 and a sinkhorn epsilon of 0.03 may be selected for an exemplary loss function.

In an exemplary embodiment, once an exemplary deep learning model is trained, it may be utilized to extract exemplary features from an exemplary thymus region of the scans. In an exemplary embodiment, 4,096 exemplary features may be extracted and these exemplary features may comprise high-dimensional embeddings that encapsulate various properties of the thymus as learned by an exemplary foundation model.

In an exemplary embodiment, saliency analysis and Shapley value analysis may be utilized to better understand how the AI makes its predictions about thymus health.

In an exemplary embodiment, Saliency Analysis may refer to an exemplary method which may help in identifying which parts of the image the AI focuses on when making a prediction. It highlights the most important regions that influence the AI's decision.

In an exemplary embodiment, Shapley Value Analysis may refer to a technique from game theory that may assign an importance score to each feature in an exemplary model's predictions. It measures how much each feature contributes to the final prediction by considering all possible combinations of features and their contributions. In simpler terms, Shapley values show how important each feature is in determining the model's output. The Shapley value of a feature represents the average marginal contribution of that feature across all possible permutations of features.

In an exemplary embodiment, an exemplary technique called occlusion sensitivity may be utilized to see which parts of the image were most important for an exemplary foundation model's prediction. In an exemplary embodiment, this may involve systematically hiding different parts of the image to see how an exemplary model's predictions change. If hiding a part of the image causes a significant change in the model's output, that part is deemed important.

In an exemplary embodiment, an exemplary important area within an exemplary image may be visualized utilizing saliency maps, which highlight the regions of the image that the model focuses on the most when making its decision. In an exemplary embodiment, these exemplary maps may show that an exemplary foundation model concentrated mainly on the thymus itself and its outlines, while giving less attention to nearby areas like the sternum or lung tissue. In an exemplary embodiment, by utilizing saliency maps to determine quality of an exemplary model, may help ensure the quality and accuracy of the thymic health assessment by an exemplary AI system.

Accordingly, using artificial intelligence, exemplary features may be extracted which may aid in determining biomarkers which may indicate health of an exemplary organ.

Now referring back to FIG. 2, step 204 comprises generating a classifying model. In an exemplary embodiment, generating the classifying model comprises generating a quality control (QC) model and generating a score model.

Figure 4A:
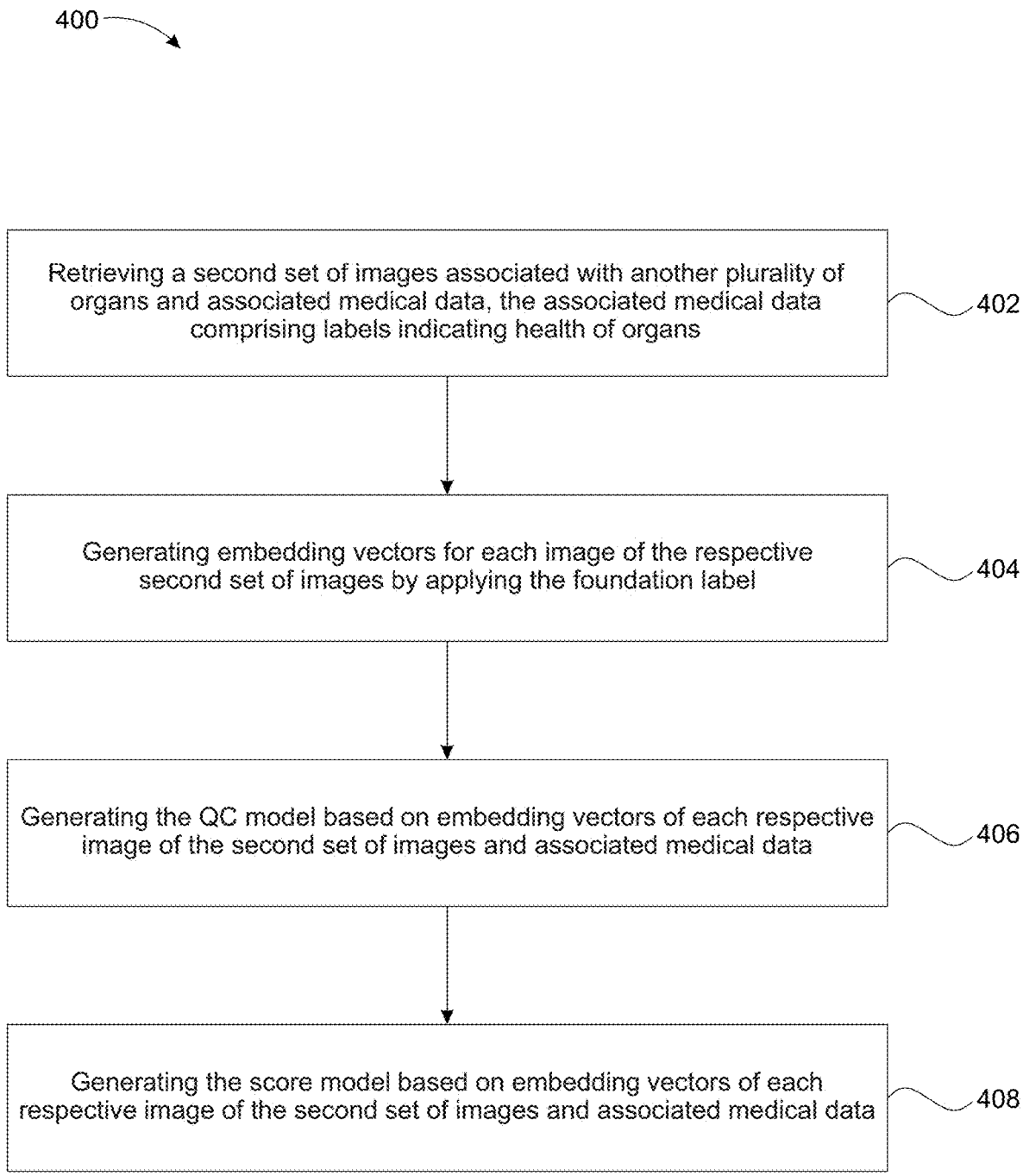
FIG. 4A illustrates a method for generating a classifying model, consistent with one or more exemplary embodiments of the present disclosure.

In an exemplary embodiment, details of step 204 are provided in method 400 of FIG. 4A. Accordingly, method 400 illustrated in FIG. 4A comprises generating a classifying model, consistent with one or more exemplary embodiments of the present disclosure. In an exemplary embodiment, generating the classifying model comprises generating a quality control (QC) model and generating a score model. In an exemplary embodiment, method 400 may comprise of steps 402 and 404.

In an exemplary embodiment, step 402 may comprise retrieving, from the one or more databases, a second set of images and associated medical data. In an exemplary embodiment, the second set of images associated may be associated with the same type or organs as utilized for an exemplary foundation model. In this exemplary scenario, to continue the example from before, the second set of images may be medical image data, such as CT scans or images, that may be associated with thymuses. In an exemplary embodiment, the associated medical data may comprise metadata in addition to labels indicating health of organs. In an exemplary embodiment, exemplary terms "labeled", "segmented" and "contoured" may be used interchangeably and may refer to the process of identifying, defining, and delineating specific regions or features within a dataset or image, such as distinguishing different anatomical structures in medical imaging or differentiating various objects in a computer vision application. Additionally, in an exemplary embodiment, exemplary associated medical image data may include clinical data associated with an image, such as clinical outcome or health outcome based on information related to the patient, for example, a person whose image may have been taken may have had organ failure six months after an image may have been taken. In an exemplary embodiment, exemplary labels associated with each respective medical image may be entered by a user, utilizing a physical device or manually provided and associated electronically. In an exemplary embodiment, an exemplary user may include a radiologist, technician, physician, or any individual qualified to evaluate a medical image for labeling. In an exemplary embodiment, the following labels may be utilized:

0, fully fatty degeneration;
1, minimal residual soft-tissue density scattered through the thymic bed/ant-sup. mediastinum;
2, approximately 50:50 soft-tissue density and fat-density attenuation through the thymic bed/ant-sup. mediastinum;
3, predominantly soft-tissue density attenuation within the thymic bed/ant-sup. mediastinum.
7, non-fat attenuation.

In an exemplary embodiment, one of ordinary skill in the art may comprehend that additional labels may be provided, or the labels may be modified without departing from principles of exemplary embodiments of the present disclosure. Specifically, labels 0, 1, 2, and 3 provide expert analyzed insight into different degeneration of an exemplary organ (thymus) while label of 7 indicates non-fat attenuation. In further detail, in an exemplary embodiment, 0 may refer to an exemplary case where an expert (radiologist, physician, etc.) believes that there is fully fatty generation of an exemplary thymus, 1 may refer to an instance where such an exemplary expert believes that there minimal residual soft-tissue density, that is, minimal residual soft-tissue density scattered through the thymic bed/ant-sup. mediastinum less than a threshold amount, for example, less than close to fifty percent or a range of less than 45 or 40 percent, 2 may refer to medium soft-tissue density and fat-density attenuation, that is, approximately 50:50 soft-tissue density and fat-density attenuation through the thymic bed/ant-sup. mediastinum in an exemplary thymus. In an exemplary embodiment, this may range from 45 to 55 percent to provide an adequate threshold around approximately 50:50, 3 may refer to predominant soft-tissue density attenuation, that is, predominantly soft-tissue density attenuation within the thymic bed/ant-sup. mediastinum in an exemplary thymus above a certain threshold amount, for example attenuation in more than 55 percent, and 7 may refer to instances that there is non-fat attenuation.

In an exemplary embodiment, to provider further context of label of 7, non-fat attenuation may refer to structures other than the thymus or different processes that may lead to non-fat attenuation through the mediastinum, potentially mimicking thymic soft-tissue attenuation, for example, lymph nodes are distributed through the mediastinum. In an exemplary embodiment, non-fat attenuation structures (that necessitate an exemplary label of a 7) may take varying forms, from small nodularities to masses, potentially mimicking residual thymic soft tissue. In an exemplary embodiment, in context of exemplary thymus evaluation, this may be caused by neoplasms invading or forming within an exemplary mediastinum. Furthermore, exemplary non-fat attenuation structure may be labeled as such due to local or adjacent inflammation including, but not limited to, the lungs (e.g. pneumonia, neoplastic disease), the heart or pericardium, or the mediastinum itself may lead to lymphadenopathy, edematous or fibrinous changes, or fat stranding throughout the mediastinum. Additionally, surgical procedures may or may have involved mediastinum, e.g. in cardiothoracic surgery, leading to post-surgical changes, potential organ loss (thymectomy), or local scarring. In an exemplary embodiment, all of these exemplary challenges may mimic streaky and nodular thymic appearance, although they readily appear more irregular, and coarse, and may be appreciated with a more dirty local appearance. In an exemplary embodiment, in case of the high probability that inflammatory or associated changes are present in the thymic bed, it may be possible that these changes may influence the local microenvironment and, thereby, thymic functionality. Accordingly, images that reflected these were provided a score of 7 (to clearly flag them as distinct from the regular thymus grading categories) for further investigation as visually thymic-grading exempt individuals. In an exemplary embodiment, reasoning for scoring of 7 for above-mentioned scenario will be further clarified in context of details with regards to generation of QC model as described in detail with respect to step 404 below.

In an exemplary embodiment, step 404 may comprise generating a task-specific classifying model, based on the foundation model, second set of images, and associated medical data. In an exemplary embodiment, an exemplary task specific classifying model may comprise generating a QC model and an exemplary score model.

In an exemplary embodiment, an exemplary QC model or an exemplary score model may both use logistic regression, that is, an exemplary QC model and an exemplary score model may be generated by training exemplary logistic regression models.

In an exemplary embodiment, other potential types of supervised learning models may be utilized for exemplary classifying models including linear regression, decision trees, classification and regression trees, Naïve Bayes, support vector machines, K-nearest neighbors, and neural networks (includes conditional random fields, convolutional neural networks, attention-based neural networks, deep learning, long short-term memory networks, or other neural models.

In an exemplary embodiment, logistic regression may refer to a statistical method used for binary classification tasks, where the goal is to predict the probability of a binary outcome based on one or more predictor variables. In an exemplary embodiment, logistic regression models the relationship between the input features and the binary response using the logistic function, which maps any real-valued number into a value between 0 and 1. In an exemplary embodiment, this probability may then be thresholded to assign a class label. In an exemplary embodiment, logistic regression is particularly useful because it not only provides class predictions but also quantifies the uncertainty of these predictions through the probability scores. In an exemplary embodiment, an exemplary model utilizing logistic regression may estimate the coefficients for each input feature through maximum likelihood estimation, ensuring that the predicted probabilities align as closely as possible with the observed outcomes in the training data.

In an exemplary embodiment, with further detail to step 404, step 404 may contain steps 406, step 408, and steps 410.

In an exemplary embodiment, in detail with respect to step 404, with regards to generating a QC model or a score model, the generating process may first comprise step 406, which may comprise generating embedding vectors, utilizing the one or more processors, for each of the retrieved second set of images based on the foundation model. In an exemplary embodiment, before step 404, pre-processing similar to pre-processing of step 304 of method 300 may be applied to medical image data in the second set of images thus producing a pre-processed second set of images so the parameters align with the training sets provided to an exemplary foundation model.

Accordingly, in an exemplary embodiment, step 406 may comprise generating an embedding vector for each respective image of the retrieved second set of images by applying a foundation model on each of the pre-processed images. In further detail, in an exemplary embodiment, an exemplary foundation model generated (for example in step 202) may be utilized to extract features from an exemplary thymus region of an exemplary scan for which medical image data is received. In an exemplary embodiment, utilizing some or all of the extracted features, an exemplary foundation model may generate or predict an embedding vector.

Figure 4B:
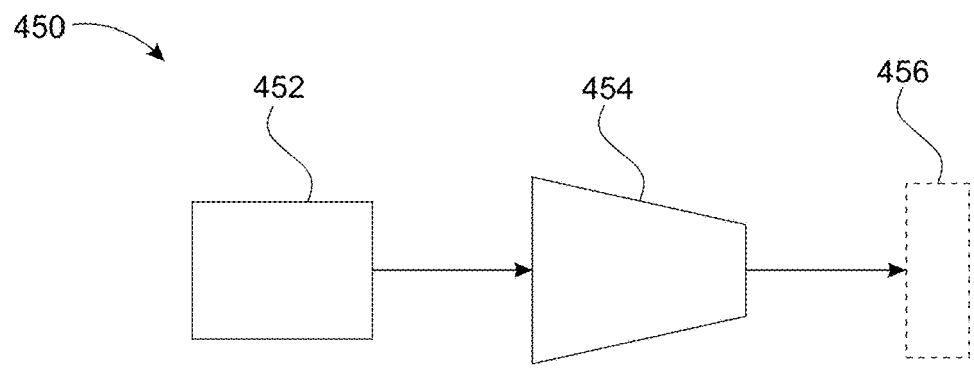
FIG. 4B illustrates a block diagram of an inference phase of a foundation model generating embedding vectors, consistent with one or more exemplary embodiments of the present disclosure.

In an exemplary embodiment, FIG. 4B displays a block diagram 450 of an exemplary process for generating an embedding vector, consistent with one or more exemplary embodiments of the present disclosure. In an exemplary embodiment, an exemplary image 452 may be provided to encoder 454. In an exemplary embodiment, exemplary image 452 may be an exemplary image after pre-processing, while encoder 454 may refer to an exemplary foundation model, such as, an exemplary foundation model generated in step 202. In an exemplary embodiment, an exemplary foundation model may have been generated for a similar organ as related to images in the exemplary second set of images, for example, exemplary foundation model and second set of images may all be related to a singular type of organ, such as an exemplary thymus. In an exemplary embodiment, an exemplary foundation model may determine/generate and output an embedding vector 456 associated with each respective image of the second set of images. That is, utilizing an exemplary foundation model, for example, such as one generated in step 202, embedding vectors may be generated for each of the images of the second set of images. Accordingly, a set of embedded vectors corresponding to the second set of images may be created where there are embedded vectors associated with each of the respective images in the second set of images may be created.

In an exemplary embodiment, due to input and use of associated medical data comprising labels along with medical image data (each respective image or scan), training of an exemplary task-based classification model comprising both an exemplary QC model and an exemplary score model may be referred to as supervised learning. That is, as described in further detail below, for each respective image from the second set of images, provided to each of a respective exemplary score model and a respective exemplary score model, embedding vectors are provided for the respective image and respective labels associated with the respective image are provided as input.

In an exemplary embodiment, as discussed above, embedding vectors generated for each respective image may further be associated with labels associated with each of the respective images, so that only embedding vectors and labels may be provided as inputs to an exemplary QC or exemplary score model.

In an exemplary embodiment, step 408 may comprise training an exemplary QC model, consistent with one or more exemplary embodiments of the present disclosure. In an exemplary embodiment, the QC model may be generated based on embedding vectors of each respective image of the second set of images and associated medical data.

For further details with respect to training an exemplary QC model, in an exemplary embodiment, an exemplary QC model may be trained and generated utilizing artificial intelligence which may utilize logistic regression. In an exemplary embodiment, generating the QC model comprises training a logistic regression model based on the embedding vectors of each respective image of the second set of images and the associated medical data.

Figure 4C:
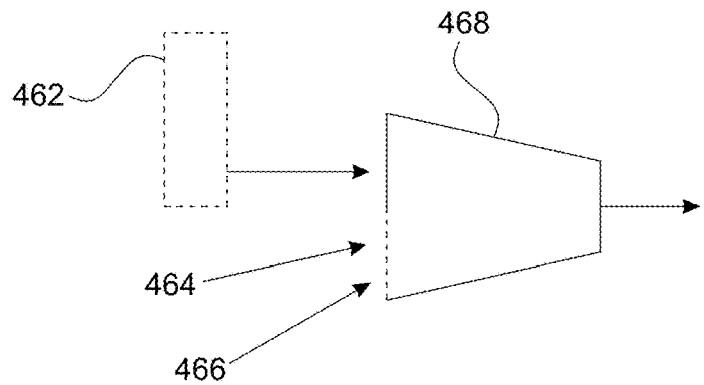
FIG. 4C illustrates a block diagram of a training phase of a QC model for determining health of an organ, consistent with one or more exemplary embodiments of the present disclosure.

In an exemplary embodiment, FIG. 4C displays a block diagram 460 of an exemplary process for training an exemplary QC model, consistent with one or more exemplary embodiments of the present disclosure. In an exemplary embodiment, for each respective image of the second set of images, an embedding vector 462 may be provided along with one of two possible inputs inflamed 464 or not inflamed 466 to classifier 468. In an exemplary embodiment, input inflamed 464 may be labeled as "7" and input of not inflamed 466 may be a collective "zero" as described in further detail below. In an exemplary embodiment, classifier 468 may be an exemplary logistic regression model. In an exemplary embodiment, utilizing these respective inputs provided to an exemplary logistic regression model, an exemplary QC model may be generated and trained.

In further detail, with respect to exemplary inputs 464 and 466, in an exemplary embodiment, labels may be categorized in a binary manner. In an exemplary, that is all images labeled 0, 1, 2, and 3 may be for the training of an exemplary QC model may be considered as a collective "zero" (for non-inflamed 466) while images labeled with a 7 may be considered as affirmative binary number, that is, when it is a 7, it may be considered that an exemplary thymus is inflamed (inflamed 464). In an exemplary embodiment, an exemplary computing system or one or more processors may apply mapping so that the labels are exemplary mapped to either being a zero (when labels are 0, 1, 2, 3) or 7 in the currently exemplary scenario. In an exemplary embodiment, 7 is chosen but any other value may have been assigned instead of the label of 7 as an affirmative value. Accordingly, in an exemplary embodiment, based on having data related to a plurality of images including embedding vectors along with labels, associated with each respective image may be utilized to generate a model which may predict that an exemplary thymus is inflamed (would be assigned a score of 7) or not inflamed (would be assigned a score of 0, 1, 2, 3) based on the labels provided for training. In an exemplary embodiment, by first determining embedding vectors and considering the assigned labels based on expert input, a QC model may be able to predict a label that should be assigned to a respective organ based on applying logistic regression to all medical image data associated with the second set of images. Therefore, in an exemplary embodiment, an exemplary QC model may therefore be configured to provide a probability on an inflamed organ by way of an exemplary value that may be provided as an output. Accordingly, if the probability of an inflamed organ is 70 percent and an exemplary score is to range from 0 to 1, then an exemplary output of a QC model may be 0.7.

In an exemplary embodiment, step 410 may comprise training an exemplary score model, consistent with one or more exemplary embodiments of the present disclosure. In an exemplary embodiment, the score model may be generated based on embedding vectors of each respective image of a chosen set of the second set of images and associated medical data. In an exemplary embodiment, generating the score model may comprise training a second logistic regression model based on the embedding vectors of each respective image of a chosen set of the second set of images and the associated medical data In an exemplary embodiment, an exemplary chosen set may refer to scans from the second set of images or scans whose labels may fall within a first category of labels. In detail, in an exemplary embodiment, for an exemplary score model, all images labeled with "7" (that is, it is inflamed) may be eliminated and remaining images with labels classifying an exemplary organ, for example, a thymus are considered. Therefore, in an exemplary embodiment, only images labeled 0, 1, 2, and 3 in the second set of images may be utilized for training an exemplary score model, and these images may be referred to as non-eliminated second set of images or the chosen set of the second set of images, that is, the first category referring to labels that may be labeled 0, 1, 2, and 3. In an exemplary embodiment, that is, an exemplary score model may be trained utilizing embedding vectors along with associated labels for each respective image of the non-eliminated second set of images.

Figure 4D:
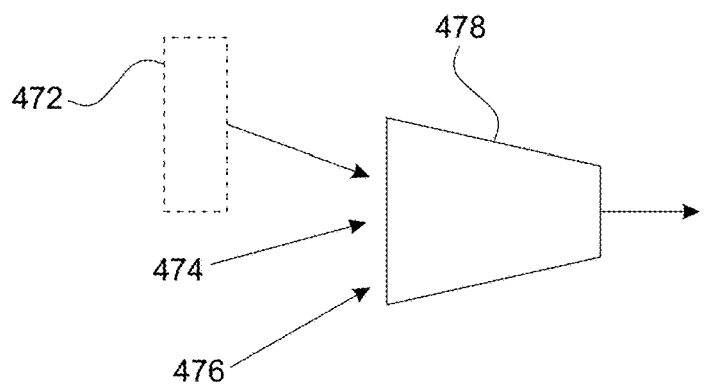
FIG. 4D illustrates a block diagram of a training phase of a score model for determining health of an organ, consistent with one or more exemplary embodiments of the present disclosure.

In an exemplary embodiment, FIG. 4D displays a block diagram 470 of an exemplary process for training an exemplary score model, consistent with one or more exemplary embodiments of the present disclosure. In an exemplary embodiment, for each respective image of the non-eliminated second set of images, an embedding vector 472 may be provided along with one of two possible inputs, input 474 or input 476 to classifier 478. In an exemplary embodiment, input 474 may be a "0" to indicate a complete fatty degeneration of an exemplary thymus. In an exemplary embodiment, input 476 may be a "1" indicating presence of thymic tissue, that is, any label comprising 1, 2, and 3 is mapped to be labeled as "1" for an input to classifier 478. In an exemplary embodiment, mapping may be applied by one or more exemplary processors, to convert any label that is a 1, 2, or 3, to be labeled as a "1" so that the input that is provided to an exemplary classifier, such as classifier 478 may be a 0 or a 1. In an exemplary embodiment, classifier 478 may be an exemplary logistic regression model. In an exemplary embodiment, utilizing these respective inputs to an exemplary logistic regression model, an exemplary score model may be generated and trained.

In further detail, and to further an exemplary scenario, as discussed above, along with exemplary images of an exemplary thymus, exemplary labels may be input. As discussed above, exemplary labels may be input by a physician or a technician. In an exemplary embodiment, for non-eliminated second set of images, respective images may be scored from 0 to 3, indicating increasing thymus health. In an exemplary embodiment, these labels may be compressed into a binary prediction model, that is, 0 remains 0, but labels that may be 1, 2, and 3, may be forced into a singular binary value such as a 1, that is, using a computing device, manual labeling, or utilizing one or more processors, 1, 2, and 3, may be mapped into a 1, similar to as done for exemplary QC model. Accordingly, as exemplary inputs, an exemplary scoring model may consider images labels as 0, 1, 2, 3, as either an exemplary "0" (for example, as input 474) or exemplary "1" (for example, as input 476). Accordingly, in an exemplary embodiment, for training of an exemplary score model, utilizing logistic regression between embedding vectors and binarized labels, score models may be formed to predict an exemplary score model. Accordingly, an exemplary score model may be trained to indicate whether the value based on an embedding vector based on medical image data would be 0 or 1.

Accordingly, in an exemplary embodiment, an exemplary score model may evaluate the level of fat and soft tissue in the thymus. More fat indicates a less healthy thymus, with 0 representing the least healthy. In an exemplary embodiment, an exemplary score model may provide a probability on health of an organ by way of an exemplary score that may be provided as an output. Accordingly, if the probability of healthy organ (that is, the probability of full tissue) is 90 percent and an exemplary score is to range from 0 to 1, then an exemplary output of an exemplary score model may be 0.9. In other words, 0 may indicate full fat while 1 may indicate full tissue.

In an exemplary embodiment, classifying model of step 204 which utilizes exemplary foundation model generated in step 202, may be utilized to predict health status and/or outcomes based on clinical approaches of an exemplary organ based on a single CT scan of an exemplary organ.

To summarize, in an exemplary embodiment, an exemplary QC model may be utilized to mark inflammation, which is not a part of normal age-related degradation. In an exemplary embodiment, inflammation may be a sign of poor immune health so due to inflammation, a low value may be provided as an output.

Figure 5A:
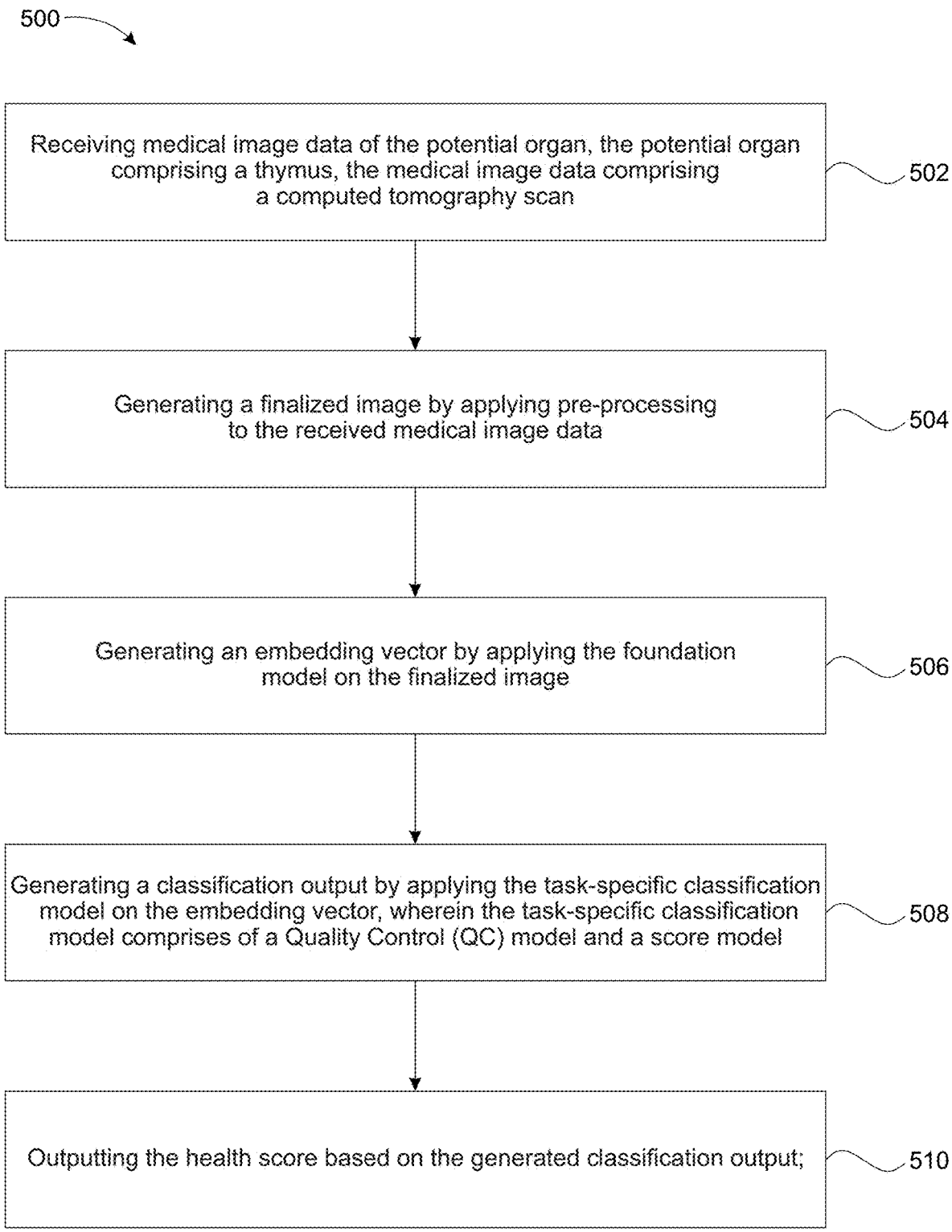
FIG. 5A illustrates a method for evaluating health of a potential organ based on medical image data, consistent with one or more exemplary embodiments of the present disclosure.

Now referring back to method 200, method 200 may further comprise of step 206. In an exemplary embodiment, step 206 may comprise evaluating health of a potential organ based on medical image data, consistent with one or more exemplary embodiments of the present disclosure. FIG. 5A illustrates method 500 which provides the details of step 206.

In an exemplary embodiment, method 500 may comprise of step 502. In an exemplary embodiment, step 502 may comprise of receiving medical image data of the potential organ. For example, an image or an exemplary CT scan of a patient's thymus may be taken in a clinical setting to determine its quality and to determine an approach to medical treatment, if necessary.

The captured image may be uploaded to a cloud environment or transferred to a computing system using a network or other methods. In an exemplary embodiment, it may be transmitted to service provider environment 130.

In an exemplary embodiment, settings and/or conditions for capturing an image of a potential endometrium may be the same as the previously captured images referred to in step 202 which were captured from an CT machine. That is, in an exemplary embodiment, capturing an image of an object of interest, such as an exemplary thymus may be conducted in similar manner and specification as capturing of the training data sets utilized for creating respective models in steps 202 and 204. In an exemplary embodiment, this may allow for more efficiency and accuracy in predictive accuracy of exemplary systems.

In an exemplary embodiment, method 504 may comprise of preparing a finalized image by applying pre-processing to the received medical image data. In an exemplary embodiment, applying pre-processing to the new image may be similar to the pre-processing applied in some of or all aspects similar to pre-processing in step 302. Accordingly, after exemplary pre-processing is applied to an image so that it is standardized similarly to CT scans that were utilized for training exemplary foundation model and task-specific classification models to be utilized on received medical image data.

In an exemplary embodiment, as described in further detail previously, pre-processing of the captured image data may comprise cropping the captured image data so that the potential organ is the focus of the image. In an exemplary embodiment, the captured image may be cropped with an exemplary organ in the center.

In an exemplary embodiment, method 500 may further consist of step 506. In an exemplary embodiment, step 506 may comprise generating an embedding vector by applying a foundation model on the finalized image. In further detail, in an exemplary embodiment, an exemplary foundation model generated (for example in step 202) may be utilized to extract features from an exemplary thymus region from the finalized image. In an exemplary embodiment, utilizing some or all of the extracted features, an exemplary foundation model may generate an embedding vector. In an exemplary embodiment, embedding vectors may be generated utilizing approaches consistent with requirements for SwAV frameworks.

Figure 5B:
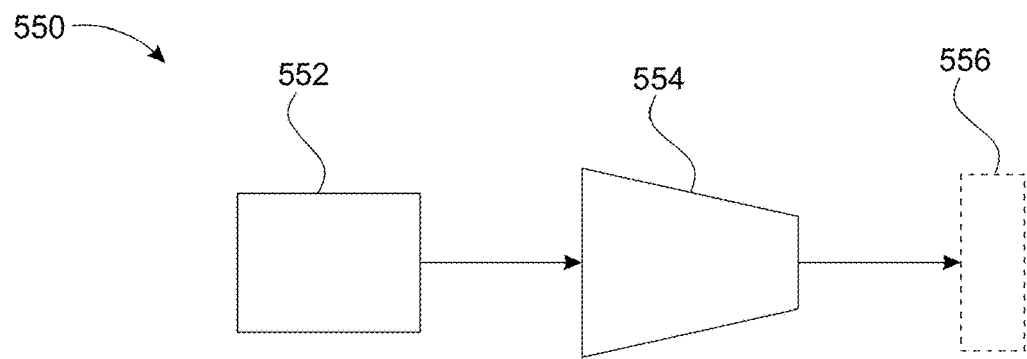
FIG. 5B illustrates a block diagram of an inference phase of a foundation model generating an embedding vector for determining health of an organ, consistent with one or more exemplary embodiments of the present disclosure.

In an exemplary embodiment, FIG. 5B displays a block diagram 550 of an exemplary process for generating an embedding vector, consistent with one or more exemplary embodiments of the present disclosure. In an exemplary embodiment, an exemplary image 552 may be provided to encoder 554. In an exemplary embodiment, exemplary image 552 may be an exemplary finalized image that may be generated by applying pre-processing as done in step 504, while encoder 554 may refer to an exemplary foundation model, such as, an exemplary foundation model generated in step 202. In an exemplary embodiment, an exemplary foundation model may have been generated for a similar organ as an image captured in an exemplary new image to be evaluated, for example, exemplary models and an exemplary new image are related to respective thymus. In an exemplary embodiment, an exemplary foundation model may determine/generate and output an embedding vector 556 associated with the finalized image.

In an exemplary embodiment, method 500 may further consist of step 508. In an exemplary embodiment, steps 508 may comprise of generating a classification output by applying the task-specific classification model on the embedding vector, wherein the task-specific classification model comprises a Quality Control (QC) model and a score model. In an exemplary embodiment, an exemplary task-specific classification model may be similar to task-specific classification model generated in step 206 comprising an exemplary QC model and exemplary score model.

In an exemplary embodiment, QC model and score model may be applied simultaneously and in parallel. In an exemplary embodiment, only one of QC model or score model may be applied. In an exemplary embodiment, an exemplary QC model may provide an exemplary output with binary predictions with probabilities differentiating between normal thymus degradation and abnormalities, while an exemplary score model may provide probabilities reflecting a level of fat and soft tissue in the thymus. Accordingly, in an exemplary embodiment, a classification output may be a dual output both from an exemplary score model and an exemplary QC model. In an exemplary embodiment, step 510 (described in further detail below) may be a part of step 510 and, therefore, an exemplary health score may be directly output based outputs of respective exemplary score and QC model.

Figure 5C:
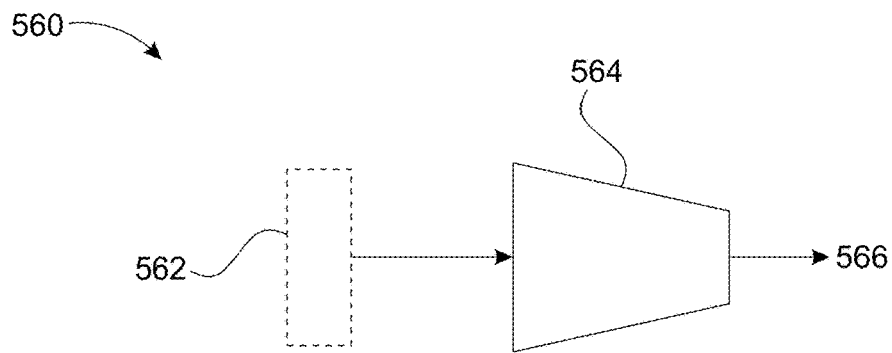
FIG. 5C displays a block diagram of an exemplary process for applying a QC model, consistent with one or more exemplary embodiments of the present disclosure.

In an exemplary embodiment, FIG. 5C displays a block diagram 560 of an exemplary process for applying a QC model, consistent with one or more exemplary embodiments of the present disclosure. In an exemplary embodiment, embedding vector 562 may be provided to classifier 564, which may output a label 566. In an exemplary embodiment, embedding vector 562 may be the same as embedding vector 556 produced utilizing an exemplary foundation model. In an exemplary embodiment, classifier 564 may refer to an exemplary QC model, such as, an exemplary QC model generated in step 204. In an exemplary embodiment, an exemplary QC model may deal with a similar organ as an image captured in an exemplary new image to be evaluated, for example, exemplary models and an exemplary new image are related to respective thymus. In an exemplary embodiment, an exemplary QC model may determine/generate an output label 566. In an exemplary embodiment, an exemplary output label may be an exemplary prediction of inflammation or not of an exemplary organ (such as a thymus) in an exemplary new image.

Figure 5D:
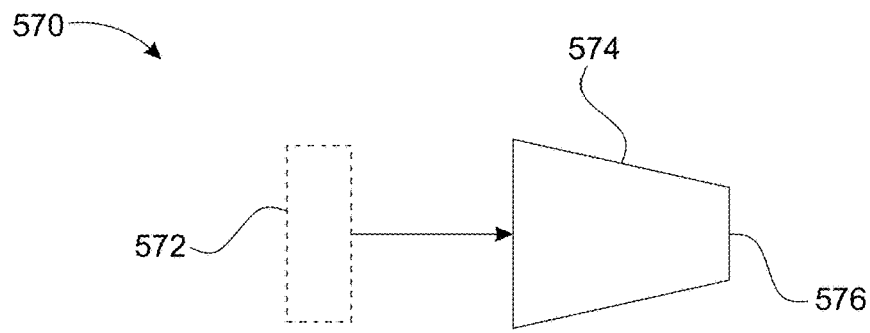
FIG. 5D displays a block diagram of an exemplary process for generating applying a score model, consistent with one or more exemplary embodiments of the present disclosure.

In an exemplary embodiment, FIG. 5D displays a block diagram 570 of an exemplary process for applying a score model, consistent with one or more exemplary embodiments of the present disclosure. In an exemplary embodiment, embedding vector 572 may be provided to classifier 574, which may output a label 576. In an exemplary embodiment, embedding vector 562 may be the same as embedding vector 556 produced utilizing an exemplary foundation model (and therefore, also 562). In an exemplary embodiment, classifier 564 may refer to an exemplary score model, such as, an exemplary score model generated in step 204. In an exemplary embodiment, an exemplary score model may deal with a similar organ as an image captured in an exemplary new image to be evaluated, for example, exemplary models and an exemplary new image are related to respective thymus. In an exemplary embodiment, an exemplary score model may determine/generate an output label 576.

Accordingly, for each of QC model or score model, based on an exemplary embedding vector value, the relevant classifying model may correlate various probabilities based on previous training sets, and the results may be generated to be output. Accordingly, an exemplary QC model may provide a first output and an exemplary score model may provide a second output.

In an exemplary embodiment, method 500 may further consist of step 510. In an exemplary embodiment, steps 510 may comprise of outputting a health score based on the generated classification output. In an exemplary embodiment, an exemplary output label of a QC model, such as output 566, may be an exemplary prediction of inflammation or not of an exemplary organ (such as a thymus) in an exemplary new image.

In an exemplary embodiment, an exemplary scenario is described where an exemplary score may be calculated for example, when an exemplary QC model has an output, for example, output 566 of 0.5 and an exemplary score model has an output, for example, output 576 of 0.7.

In an exemplary embodiment, if an exemplary QC model has an output above a certain threshold, then there may be a high certainty of inflammation, therefore an exemplary output of a score model may be discarded. That is, a value of output 566 is above a threshold value, output 576 from an exemplary score model may be discarded.

In an exemplary embodiment, if the value of output 566 is below an exemplary threshold value, then there is a high certainty of lack of inflammation. In such an instance, an exemplary output of the classification model is the output of an exemplary score model, such as output 576.

Accordingly, in an exemplary embodiment, QC model may be utilized as a quality check or an exemplary gate/filter to an output of an exemplary score model.

In an exemplary embodiment, to continue to exemplary scenario as presented above, QC model output of 0.5 and a score model output of 0.7 with an exemplary inflammation threshold of 0.9 would mean no inflammation. In such an exemplary case, the score model output of 0.7 may be output as an exemplary health score.

In an exemplary embodiment, an exemplary score may be calculated from the output of classifying model. In an exemplary embodiment, an exemplary health score may fall on a prespecified scale and may be a number between 0 to 1, 0 to 10, or 0 to 100 or can be a percentage from 0% to 100%, or may range from 0 to a certain number, with the lowest value denoting a weak immune system and the highest score denoting a strong immune system. In an exemplary embodiment, an exemplary scale may be calibrated on a population of interest based on percentile ranks to increase interpretability and facilitate application for dedicated use cases.

In an exemplary embodiment, an exemplary score may be primarily determined based on output of an exemplary score model, with exceptions (or quality control) based on output of an exemplary quality control (QC) model.

In an exemplary embodiment, an exemplary QC model may be optimized to identify causes other than thymic tissue that may lead to non-fat attenuation in the thymic bed, such as fat stranding or scar tissue. In an exemplary embodiment, these other causes may have appearances that may mimic thymic tissue and thereby may potentially bias an exemplary score model. Accordingly, an exemplary QC model may assess scans for signs of cancer or abnormalities and provide an exemplary output.

In an exemplary embodiment, to increase robustness of an exemplary score, an exemplary QC model identifies these cases if a high likelihood of these issues is detected, and accordingly, scoring model output may be assigned a very low value, close to zero, that is, an equivalent score of zero plus some gaussian noise may be added, for example, of less than ten percent of a total possible value may be assigned as an exemplary health score.

In an exemplary embodiment, an exemplary threshold for detecting abnormalities in an exemplary QC model may be set based on epidemiological estimates and primarily through trial and error using data from an independent set of scans with associated medical data. In an exemplary embodiment, within healthy individuals, which may be equal to ninety-five percent of generally scanned cases, a final score may be input based on output of an exemplary scoring model without being impacted by output of an exemplary QC model. That is, in the other 5 percent of cases, a final score may be provided based on an output of an exemplary QC model without being impacted by output of an exemplary score model. However, in other instances with individuals with likely worse health, for example, multimorbid individuals with high probabilities of mediastinal alteration, for example. cancer patients after mediastinal radiotherapy, in twenty-five percent of instances, an exemplary output of a QC model may lead to an output of an exemplary score model to be negated.

In an exemplary embodiment, an exemplary assigned score may be interpreted utilizing an exemplary prespecified scale. In an exemplary embodiment, this exemplary prespecified scale may include threshold value(s) that may be used to interpret an exemplary health score. For example, exemplary scores above, at, or below the threshold(s) indicate different outcomes e.g., three threshold buckets <33%, 34%-67%, and >68% to indicate a weak, moderate, and strong immune health, respectively.

In an exemplary embodiment, an exemplary health score generated by an exemplary service provider may refer to an exemplary health score referring to a particular organ such as an exemplary health score for a thymus, spleen, bone marrow, etc. In an exemplary embodiment, service provider associated with service provider environment 130 may be able to generate a single overall immune health score comprising some or all immune organs and may be present with this score taking into account all underlying organs either with equal or unequal weights.

In an exemplary embodiment, health scores may be generated at different time points (based on images or scans taken at different timepoints) and may be aggregated to produce a trend. In an exemplary embodiment, an exemplary difference (delta) between scores generated at different time points may be used as an indicator for improving, declining, or stable immune health.

Returning back to FIG. 2, method 200 may further comprise applying a clinical solution based on the evaluated health of the potential organ based on a health score. In an exemplary embodiment, one or more exemplary processors associated with an exemplary physician or service provider may provide a clinical solution based on the health score. In detail, in an exemplary embodiment, an exemplary service provider may provide along with an exemplary health score, explanation of results and limitations, treatment recommendations, clinical trial recommendations, incorporation of other biomarkers, and providing a contextual perspective of an exemplary patient compared to a larger distribution.

In an exemplary embodiment, an exemplary health score may be utilized used alone or combined with other preexisting and validated patient data and biomarkers generated for a given subject (e.g., sex, gender, age, smoking status, Programmed-Death Ligand 1 (PD-L1), Tumor Mutation Burden (TMB)). Depending on clinical needs, an exemplary score may be used alone (no established biomarker, emergency decisions without time to wait for established biomarker turnaround times) or in combination with established biomarkers to guide clinical decision-making and together they may provide clinical recommendations. In an exemplary embodiment, a clinical solution such as whether to apply immunological approaches, chemotherapy approaches, surgical approaches, radiotherapy approaches, and combination thereof, or none may be decided upon an exemplary score.

For example, in an exemplary scenario, applying a clinical solution based on the health score may comprise applying chemotherapy and immunotherapy in response to a low health score. In an exemplary embodiment, a low health score may be an amount below a certain threshold such as thirty-three percent of a possible highest score of the health score. In another exemplary scenario, applying a clinical solution based on the health score Furthermore, in an exemplary scenario, applying a clinical solution based on the health score may comprise applying only immunotherapy in response to a high health score. In an exemplary embodiment, a high health score may be an amount above a certain threshold such as sixty-six or sixty-seven percent of a possible highest score of the health score.

For example, in an exemplary embodiment, in response to a middle score, that is between thirty-three percent and sixty-seven percent, clinical solution may be either immunotherapy or combination of immunotherapy and chemotherapy, but may be further guided by additional exemplary models which may rely on other factors such as age, weight, or other medically relevant conditions of exemplary patients.

In an exemplary embodiment, based on an exemplary health score, an exemplary clinician may decide on monitoring strategy for a patient, that is, a person who does not have a high health score may have more regularized checkups or screenings. Additionally, additional and/or suggestions in change of diet, exercise, or other preventive measures may be provided such as dietary supplements for immune function and infectious diseases. Furthermore, in exemplary embodiments individuals with low immune score may be referred to referred to undergo additional immune-related tests though other non-radiographic imaging means e.g. biopsy (pathology or genomics).

In an exemplary embodiment, for patients with high immune scores, it may be important to spare the immune organs from unnecessary radiation. Accordingly, exemplary treatment plans may be adjusted to radiate the immune organs with as low a radiation dosage as technically possible.

Figure 6:
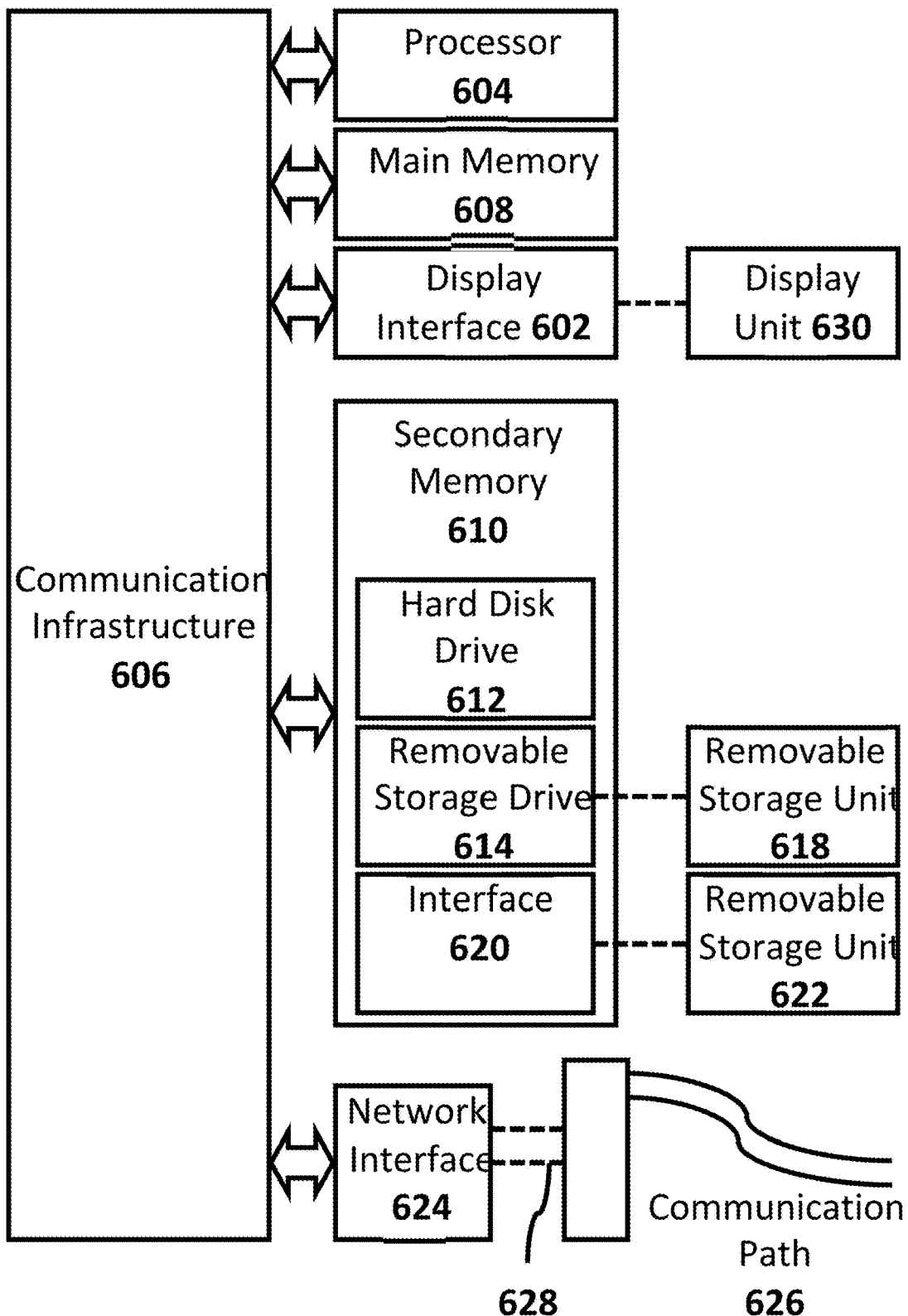
FIG. 6 illustrates an example computer system in which an embodiment of the present invention, or portions thereof, may be implemented as computer-readable code, consistent with exemplary embodiments of the present disclosure.

FIG. 6 illustrates an example computer system 600 in which an embodiment of the present invention, or portions thereof, may be implemented as computer-readable code, consistent with exemplary embodiments of the present disclosure. For example, device 100 may be implemented in computer system 600 using hardware, software, firmware, tangible computer readable media having instructions stored thereon, or a combination thereof and may be implemented in one or more computer systems or other processing systems. Hardware, software, or any combination of such may embody any of the modules and components utilized with respect to the methods described in FIGS. 2-5D.

If programmable logic is used, such logic may be executed on a commercially available processing platform or a special purpose device. One of ordinary skill in the art may appreciate that an embodiment of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

For instance, a computing device having at least one processor device and a memory may be used to implement the above-described embodiments. A processor device may be a single processor, a plurality of processors, or combinations thereof. Processor devices may have one or more processor "cores."

An embodiment of the invention is described in terms of this example computer system 600. After reading this description, it will become apparent to a person skilled in the relevant art how to implement the invention using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

Processor device 604 may be a special purpose or a general-purpose processor device. As will be appreciated by persons skilled in the relevant art, processor device 604 may also be a single processor in a multi-core/multiprocessor system, such system operating alone, or in a cluster of computing devices operating in a cluster or server farm. Processor device 604 is connected to a communication infrastructure 606, for example, a bus, message queue, network, or multi-core message-passing scheme.

Computer system 600 also includes a main memory 608, for example, random access memory (RAM), and may also include a secondary memory 610. Secondary memory 610 may include, for example, a hard disk drive 612, removable storage drive 614. Removable storage drive 614 may comprise a floppy disk drive, a magnetic tape drive, an optical disk drive, a flash memory, or the like. The removable storage drive 614 reads from and/or writes to a removable storage unit 618 in a well-known manner. Removable storage unit 618 may comprise a floppy disk, magnetic tape, optical disk, etc., which is read by and written to by removable storage drive 614. As will be appreciated by persons skilled in the relevant art, removable storage unit 618 includes a computer usable storage medium having stored therein computer software and/or data.

In alternative implementations, secondary memory 610 may include other similar means for allowing computer programs or other instructions to be loaded into computer system 600. Such means may include, for example, a removable storage unit 622 and an interface 620. Examples of such means may include a program cartridge and cartridge interface (such as that found in video game devices), a removable memory chip (such as an EPROM, or PROM) and associated socket, and other removable storage units 622 and interfaces 620 which allow software and data to be transferred from the removable storage unit 622 to computer system 600.

Computer system 600 may also include a communications interface 624. Communications interface 624 allows software and data to be transferred between computer system 600 and external devices. Communications interface 624 may include a modem, a network interface (such as an Ethernet card), a communications port, a PCMCIA slot and card, or the like. Software and data transferred via communications interface 624 may be in the form of signals, which may be electronic, electromagnetic, optical, or other signals capable of being received by communications interface 624. These signals may be provided to communications interface 624 via a communications path 626. Communications path 626 carries signals and may be implemented using wire or cable, fiber optics, a phone line, a cellular phone link, an RF link or other communications channels.

In this document, the terms "computer program medium" and "computer usable medium" are used to generally refer to media such as removable storage unit 618, removable storage unit 622, and a hard disk installed in hard disk drive 612. Computer program medium and computer usable medium may also refer to memories, such as main memory 608 and secondary memory 610, which may be memory semiconductors (e.g. DRAMs, etc.).

Computer programs (also called computer control logic) are stored in main memory 508 and/or secondary memory 610. Computer programs may also be received via communications interface 624. Such computer programs, when executed, enable computer system 500 to implement the present invention as discussed herein. In particular, the computer programs, when executed, enable processor device 604 to implement the processes of the present invention, such as the operations in the method illustrated by flowchart 200 of FIG. 2, flowchart 300 of FIG. 3A, flowchart 400 of FIG. 4A, and flowchart 500 of FIG. 5A discussed above. Accordingly, such computer programs represent controllers of the computer system 600. Where the invention is implemented using software, the software may be stored in a computer program product and loaded into computer system 500 using removable storage drive 614, interface 620, and hard disk drive 612, or communications interface 624.

Embodiments of the invention also may be directed to computer program products comprising software stored on any computer useable medium. Such software, when executed in one or more data processing device, causes a data processing device(s) to operate as described herein. An embodiment of the invention employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, and optical storage devices, MEMS, nanotechnological storage device, etc.).

The embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments but should be defined only in accordance with the following claims and their equivalents.

Throughout this specification and the claims which follow, unless the context requires otherwise, the word "comprise", and variations such as "comprises" or "comprising", will be understood to imply the inclusion of a stated integer or step or group of integers or steps but not to the exclusion of any other integer or step or group of integers or steps.

Moreover, the word "substantially" when used with an adjective or adverb is intended to enhance the scope of the particular characteristic; e.g., substantially planar is intended to mean planar, nearly planar and/or exhibiting characteristics associated with a planar element. Further use of relative terms such as "vertical", "horizontal", "up", "down", and "side-to-side" are used in a relative sense to the normal orientation of the apparatus.

What is claimed:

1. A method for determining health of an organ based on medical image data, comprising:
   generating a foundation model, utilizing one of more processors, by:
      retrieving, from one or more databases, a set of images related to a plurality of organs, the set of images comprising CT scans related to respective thymus;
      generating a set of pre-processed images by applying pre-processing to the set of images, the pre processing comprising standardizing the set of images to an isotropic resolution and adjusting scan intensities for consistency;
      training the foundation model to predict embedding vectors, using artificial intelligence, by;
         producing embedding vectors for each image of the set of pre-processed images by utilizing a deep convolutional neural network architecture; and
         refining the embedding vectors by applying a self-supervised learning framework to the embedding vectors associated with the set of pre-processed images;
   generating a task-specific classifying model based, wherein generating the task specific classifying model comprising generating a Quality Control (QC) model and generating a score model, the QC model providing binary predictions with probabilities differentiating between normal thymus degradation and abnormalities, wherein the score model evaluating a level of fat and soft tissue in the thymus, by:
      retrieving, from the one or more databases, a second set of images associated with another plurality of organs and associated medical data, the associated medical data comprising labels indicating health of organs;
      generating, utilizing the artificial intelligence, embedding vectors for each image of the respective second set of images by applying the foundation model,
      generating, utilizing the artificial intelligence, the QC model based on embedding vectors of each respective image of the second set of images and associated medical data; and
      generating, utilizing the artificial intelligence, the score model based on embedding vectors of each respective image of a chosen set of the second set of images and associated medical data;

evaluating health of a potential organ based on medical image data, comprising:
receiving medical image data of the potential organ, the potential organ comprising a thymus, the medical image data comprising a computed tomography scan; and
generating a finalized image by applying pre-processing, using one or more processors, to the received medical image data;
generating an embedding vector by applying the foundation model on the finalized image; and
generating a classification output by applying the task-specific classification model on the embedding vector, wherein the task-specific classification model comprises of a Quality Control (QC) model and a score model, wherein generating the classification output comprises generating the classification output based on an inflammation label output by the QC model and based on the level of fat and soft tissue label output by the score model based on the embedding vector;
outputting the health score based on the generated classification output; and
applying a clinical solution based on the health score, comprising:
applying chemotherapy and immunotherapy in response to a low health score, the low health score comprising less than 33 percent of a possible highest score of the health score; and
applying immunotherapy in response to a high health score, the high health score comprising greater than 68 percent of a possible highest score of the health score.

2. The method of claim 1, wherein:
generating the QC model comprises generating the QC model based on the embedding vectors, generated utilizing the foundation model, of each respective image of the second set of images and associated medical data, the associated medical data comprising labels associated with each respective image of the second set of images; and
generating the score model comprises generating, the score model based on the embedding vectors, generated utilizing the foundation model, of each respective image of a chosen set of the second set of images and associated medical data, the associated medical data comprising labels associated with each respective image of the second set of images, the chosen set of images comprising images labeled within a first category of labels.

3. The method of claim 2, wherein:
generating the QC model comprises training a logistic regression model based on the embedding vectors of each respective image of the second set of images and the associated medical data; and
generating the score model comprises training a second logistic regression model based on the embedding vectors of each respective image of a chosen set of the second set of images and the associated medical data.

4. The method of claim 3, wherein the labels indicate a) fully fatty degeneration, b) minimal residual soft-tissue density c) medium soft-tissue density and fat-density attenuation, d) predominant soft-tissue density attenuation, and e) non-fat attenuation and are respectively labeled by assigning values of 0, 1, 2, 3, and 7 respectively.

5. The method of claim 4, wherein the labels indicate a) fully fatty degeneration, b) minimal residual soft-tissue density c) medium soft-tissue density and fat-density attenuation, d) predominant soft-tissue density attenuation, and e) non-fat attenuation and are respectively labeled by assigning values of 0, 1, 2, 3, and 7 respectively.

6. The method of claim 5, wherein training the QC model comprises training the trained logistic regression model providing binary predictions with probabilities differentiating between normal thymus degradation and abnormalities by mapping the value of 0, 1, 2, and 3 to 0, and mapping the value of 7 to an affirmative binary value.

7. The method of claim 6, wherein training the score model comprises training the trained logistic regression model evaluating a level of fat and soft tissue in the thymus by mapping the value of 1, 2, and 3 to 1, and keeping the value of 0 to 0.

8. The method of claim 1, wherein applying the pre-processing comprises adjusting the scan intensities to fit within a specific range.

9. The method of claim 8, wherein the wherein applying pre-processing further comprises one or more of:
detecting and fixing abnormalities;
confirming presence of regions of interests; and
improving image quality of the one or more images by applying AI to image resolutions and by suppressing noise.

10. A method for determining health of an organ based on medical image data, comprising:
generating, utilizing one or more processors and artificial intelligence, a foundation model, by:
retrieving, from one or more databases, a set of images related to a plurality of organs, the set of images comprising CT scans related to respective thymus;
generating, using the one or more processors, a set of pre-processed images by applying pre-processing to the set of images;
training, utilizing the artificial intelligence, the foundation model to predict embedding vectors, using artificial intelligence, by;
producing embedding vectors for each image of the set of pre-processed images by utilizing a deep convolutional neural network architecture; and
refining the embedding vectors by applying a self-supervised learning framework to the embedding vectors associated with the set of pre-processed images;
generating, utilizing the artificial intelligence, a task-specific classification model, wherein generating the task specific classification model comprises generating a Quality Control (QC) model and generating a score model, the QC model providing binary predictions with probabilities differentiating between normal thymus degradation and abnormalities, wherein the score model evaluating a level of fat and soft tissue in the thymus, by:
retrieving, from the one or more databases, a second set of images associated with another plurality of organs and associated medical data, the associated medical data comprising labels indicating health of organs;
generating, utilizing the artificial intelligence, embedding vectors for each image of the respective second set of images by applying the foundation model,
generating, utilizing the artificial intelligence, the QC model based on embedding vectors of each respective image of the second set of images and associated medical data; and
generating, utilizing the artificial intelligence, the score model based on embedding vectors of each respective image of a chosen set of the second set of images and associated medical data;

evaluating health of a potential organ based on the medical image data, comprising:

receiving the medical image data of the potential organ, the potential organ comprising a thymus, the medical image data comprising a computed tomography scan; and generating a finalized image by applying pre-processing, using one or more processors, to the received medical image data of the potential organ;

generating an embedding vector by applying the foundation model on the finalized image; and generating a classification output by applying the task-specific classification model on the embedding vector, wherein the task-specific classification model comprises of a Quality Control (QC) model and a score model, wherein generating the classification output comprises generating the classification output based on an inflammation label output by the QC model and based on the level of fat and soft tissue label output by the score model based on the embedding vector; and outputting a health score based on the generated classification output.

11. The method of claim 10, wherein the labels indicating health of organs comprises labels that indicate levels of fatty degeneration or non-fat attenuation.

12. The method of claim 10, wherein the set of labeled images comprise labels indicating the levels of fatty degeneration or non-fat attenuation in the thymus comprising labels that indicate a) fully fatty degeneration, b) minimal residual soft-tissue density c) medium soft-tissue density and fat-density attenuation, d) predominant soft-tissue density attenuation, and e) non-fat attenuation.

13. The method of claim 10, wherein the method further comprises providing a clinical solution, utilizing the one or more processors, and applying the clinical solution based on the health score.

14. The method of claim 13, wherein applying the clinical solution based on the health score comprises:

applying chemotherapy and immunotherapy in response to a low health score, the low health score comprising less than a first percentage of a possible highest score of the health score; and applying immunotherapy in response to a high health score, the high health score comprising greater than a second percentage of a possible highest score of the health score, a value of the second percentage higher than a value of the first percentage.

15. The method of claim 14, wherein the first percentage is thirty-three percent and the second percentage is sixty-eight percent.

16. The method of claim 15, further comprising outputting the health score based on the generated classification output.

* * * * *